(12) United States Patent
Hoffman

(10) Patent No.: US 11,738,948 B2
(45) Date of Patent: Aug. 29, 2023

(54) PHARMACY ORDER FILLING SYSTEM AND RELATED METHODS

(71) Applicant: Express Scripts Strategic Development, Inc., St. Louis, MO (US)

(72) Inventor: Robert E. Hoffman, Linden, IN (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 0 days.

(21) Appl. No.: 17/716,298

(22) Filed: Apr. 8, 2022

(65) Prior Publication Data

US 2022/0227581 A1 Jul. 21, 2022

Related U.S. Application Data

(63) Continuation of application No. 16/538,294, filed on Aug. 12, 2019, now Pat. No. 11,299,346.

(60) Provisional application No. 62/717,954, filed on Aug. 13, 2018.

(51) Int. Cl.
| | |
|---|---|
| *G16H 20/13* | (2018.01) |
| *B65G 1/137* | (2006.01) |
| *G16H 20/10* | (2018.01) |

(52) U.S. Cl.
CPC .......... *B65G 1/1371* (2013.01); *G16H 20/10* (2018.01); *G16H 20/13* (2018.01); *B65G 2201/027* (2013.01)

(58) Field of Classification Search
CPC ....... B65B 5/103; B65B 9/06; G07F 17/0092; G16H 20/10

USPC ........................................................ 700/216
See application file for complete search history.

(56) References Cited

U.S. PATENT DOCUMENTS

| | | | |
|---|---|---|---|
| 6,330,351 B1 | 12/2001 | Yasunaga | |
| 6,690,998 B1 | 2/2004 | Yuyama | |
| 6,799,685 B1 * | 10/2004 | Yuyama | ............. G07F 17/0092 209/552 |
| 7,706,915 B2 | 4/2010 | Mohapatra | |
| 7,765,776 B1 | 8/2010 | Leu | |
| 9,117,010 B2 | 8/2015 | Feldman | |
| 9,168,223 B2 | 10/2015 | Alfano | |
| 9,904,992 B2 | 2/2018 | Takamori | |
| 9,914,554 B2 | 3/2018 | Lokkers | |
| 10,223,504 B2 | 3/2019 | Ervin | |
| 10,322,066 B2 | 6/2019 | Thach | |
| 10,435,192 B2 | 10/2019 | Luciano, Jr. | |
| 11,299,346 B1 * | 4/2022 | Hoffman | ................. B65B 57/10 |

(Continued)

*Primary Examiner* — Timothy R Waggoner
(74) *Attorney, Agent, or Firm* — Schwegman Lundberg & Woessner

(57) ABSTRACT

Drug packets may be dispensed as a belt of drug packets. Machine-readable identifiers in the belt may be automatically read to identify drug packets and associate the drug packets with the received orders. The drug packets may be automatically inspected to confirm contents of the drug packets against the received orders. The belt may be automatically separated into segments of drug packets. Each of the segments may correspond to a supply period and each of the drug packets within each of the segments may correspond to a drug dose event for the multi-drug regimen within the supply period. The segments of the belt may be automatically accumulated into belt rolls such that, for each of the belt rolls, a first segment end is on an interior of the belt roll and a second segment end is on an exterior of the belt roll.

18 Claims, 11 Drawing Sheets

(56) References Cited

U.S. PATENT DOCUMENTS

| | | | |
|---|---|---|---|
| 2004/0123564 A1* | 7/2004 | McErlean | B65B 61/20 |
| | | | 53/445 |
| 2006/0266188 A1* | 11/2006 | Kim | B26D 7/32 |
| | | | 83/511 |
| 2008/0033027 A1 | 2/2008 | Bascomb | |
| 2012/0290129 A1* | 11/2012 | Luciano, Jr. | B65B 5/103 |
| | | | 700/244 |
| 2012/0296592 A1 | 11/2012 | Luciano, Jr. | |
| 2014/0188506 A1 | 7/2014 | Kulawiec | |
| 2014/0318078 A1 | 10/2014 | Kondo | |
| 2017/0341794 A1* | 11/2017 | Kim | B65B 57/10 |
| 2018/0218128 A1 | 8/2018 | Burrows | |
| 2019/0151196 A1 | 5/2019 | Trower | |
| 2019/0254931 A1 | 8/2019 | Thach | |

* cited by examiner

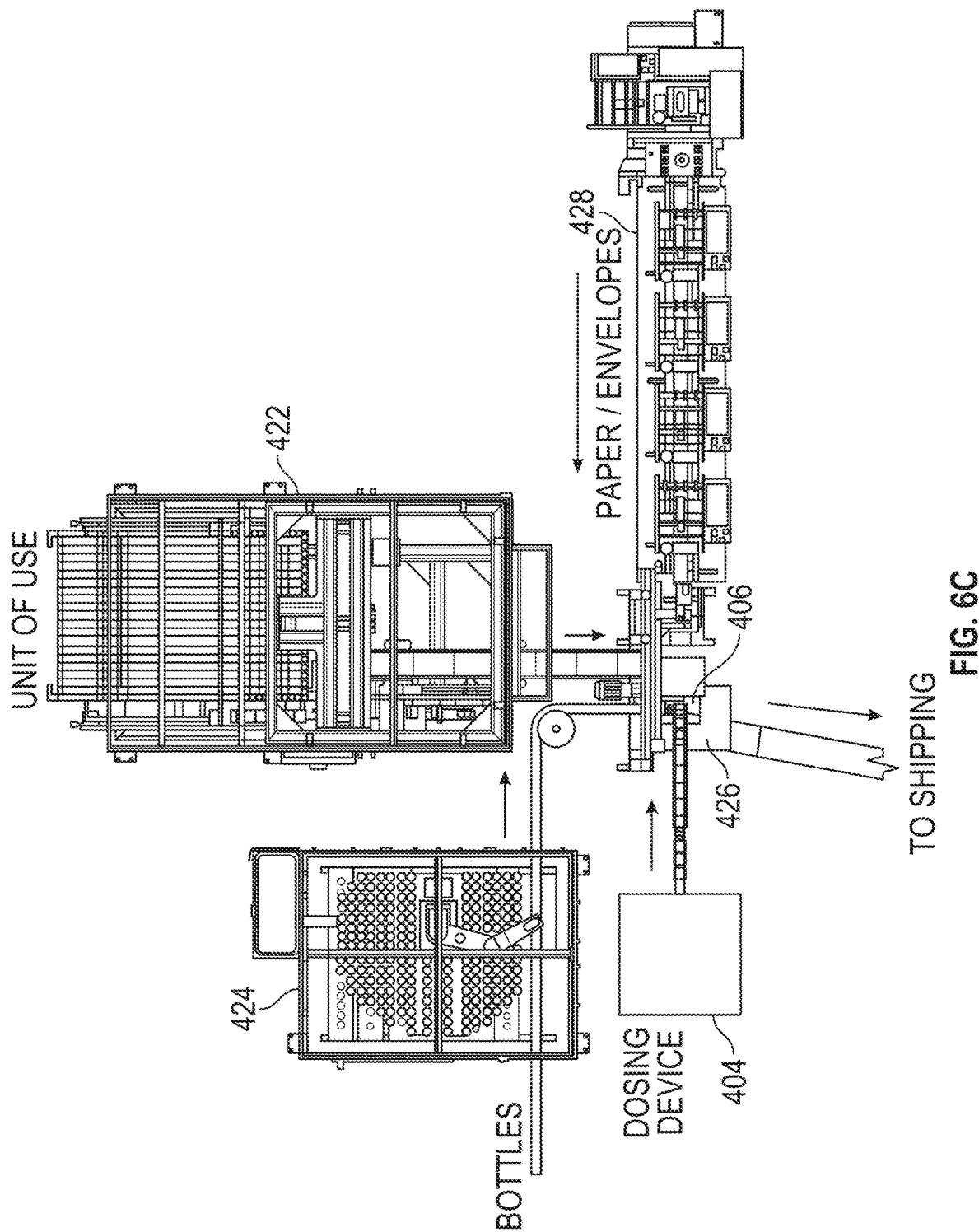

PHARMACY ORDER FILLING SYSTEM AND RELATED METHODS

CROSS REFERENCE TO RELATED APPLICATIONS

This application is a continuation of U.S. patent application Ser. No. 16/538,294 filed Aug. 12, 2019 said application claims the benefit of U.S. Provisional Application No. 62/717,954, filed Aug. 13, 2018. The entire disclosure of the above applications are incorporated by reference.

TECHNICAL FIELD

The present disclosure relates generally to automated filling centers such as a high-volume pharmacy, and more particularly, to systems, devices, and methods for filling daily dosage unit pharmacy orders within a high-volume pharmacy.

BACKGROUND

Pharmaceutical order processing systems typically involve labor intensive and/or complicated processes to sort and prepare portions of the order such that the various portions of the order may be correctly processed and/or joined up with other portions of the pharmacy order for packaging and shipment to the customer. Daily dosage unit pharmacy orders may include multiple separate daily dosage unit containers, each containing multiple pharmaceutical products to be taken by the customer at the same time. The pharmaceutical products of the daily dosage unit order or product selection are required to be dispensed accurately and in relatively small quantities to generate each of the daily dosage unit dosages, and thus the process for filling daily dosage unit orders is difficult to efficiently complete and requires substantial operator and machine time to ensure the dosages are correctly dispensed, packed, and shipped. Improved systems and methods for filling daily dosage unit pharmacy orders at a high volume to improve order fulfillment realization and customer satisfaction are needed.

This background section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

SUMMARY

This Summary includes examples that provide an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

An example of subject matter (such as a system, a device, apparatus or machine) may include an order filling system. By way of example, the order filling system may comprise an order processing device, a drug packet dispensing device, a container-identifier device, an inspection assembly and a belt accumulator. The order processing device may be configured to receive pharmaceutical orders including orders for drugs used in multi-drug regimens, respectively. Each of the multi-drug regimens may have a plurality of scheduled dosing events. The drug packet dispensing device may be configured to communicate with the order processing device, and dispense drug packets based on the received pharmaceutical orders. The drug packets may be dispensed as a belt of drug packets in which adjacent drug packets in the belt are connected. Each of the drug packets may correspond to one of the plurality of scheduled dosing events. Each of the drug packets may contain one or more of the drugs used in the multi-drug regimen for one of the plurality of scheduled dosing events. Each of the drug packets may have a machine-readable identifier identifying each of the drug packets dispensed from the drug packet dispensing device. The container-identifier device may be configured to read the machine-readable identifiers in the belt to identify drug packets and associate the identified drug packets with the received pharmaceutical orders. The inspection assembly may be configured to inspect the drug packets to confirm contents of the drug packets against the received pharmaceutical orders. The belt separator may be configured to separate the belt into segments of drug packets. Each of the segments may correspond to a supply period. Each of the drug packets within each of the segments may correspond to a drug dose event within the supply period for the multi-drug regimen. The belt accumulator may be configured to accumulate the segments of the belt into belt rolls such that, for each of the belt rolls, a first segment end is on an interior of the belt roll and a second segment end is on an exterior of the belt roll.

An example of subject matter (e.g. a method, a means for performing acts, or a machine-readable medium including instructions that, when performed by the machine, cause the machine to perform acts) may include filling orders. Pharmaceutical orders may be received using an order processing device. The pharmaceutical orders may include orders for drugs used in multi-drug regimens, wherein each of the multi-drug regimens has a plurality of scheduled dosing event. Drug packets, which may have been dispensed from a drug packet device based on the received pharmaceutical orders, may be received. The drug packets may be dispensed as a belt of drug packets in which adjacent drug packets in the belt are connected. Each of the drug packets may correspond to one of the plurality of scheduled dosing events. Each of the drug packets may contain one or more of the drugs used in the multi-drug regimen for one of the plurality of scheduled dosing events. Each of the drug packets may have a machine-readable identifier identifying each of the drug packets dispensed from the drug packet dispensing device. The machine-readable identifiers in the belt may be automatically read to identify drug packets and associate the drug packets with the received orders. The drug packets may be automatically inspected, using an inspection assembly, to confirm contents of the drug packets against the received orders. The belt may be automatically separated into segments of drug packets. Each of the segments may correspond to a supply period and each of the drug packets within each of the segments may correspond to a drug dose event for the multi-drug regimen within the supply period. The segments of the belt may be automatically accumulated into belt rolls such that, for each of the belt rolls, a first segment end is on an interior of the belt roll and a second segment end is on an exterior of the belt roll.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 6A-6C illustrate, by way of example and not limitation, views of an embodiment of the product selection order filling system shown in FIG. 4.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Generally, a prescription order or pharmaceutical order may be generated for a high-volume pharmacy, where the prescription order may include more than one prescription drug for fulfillment. For example, the prescription order may include a single prescription drug. In another example, the prescription order may include two or more prescription drugs. Each prescription drug in a prescription order may be considered to be an order component of the prescription order. Pharmaceutical orders may include orders for drugs used in multi-drug regimens. Each of the multi-drug regimens has a plurality of scheduled dosing events. For example, a dosing event may be associated with a day and/or date, and time of the day (e.g. Monday, 8:00 AM; Monday, 8:00 PM) in which one or more of the drugs are administered. The order components may correspond to the scheduled dosing events. A quantity of a prescription drug (e.g. order component) may be distributed in pill bottles, containers, or other packaging. Multiple pharmaceutical products may also be dispensed together as part of a pharmaceutical product selection for a dosing event (e.g. daily dosage unit application of similar function). The multiple pharmaceutical products that make up a drug dose event or product selection may be dispensed into a containment object, which may be referred to as a dosage unit container, and then the containment object may be transported, inspected, and packed with multiple other containment objects also containing pharmaceutical product selections for daily dosage unit applications. It is noted that a pharmaceutical order may include, in addition to the drugs used in the multi-drug regimen, other non-prescription medicines or other products that are not medicinal such as, by way of example and not limitation, bandages. These other components of the pharmaceutical order may be packaged with the scheduled dosing events of the multi-drug regimen.

Figure 1:
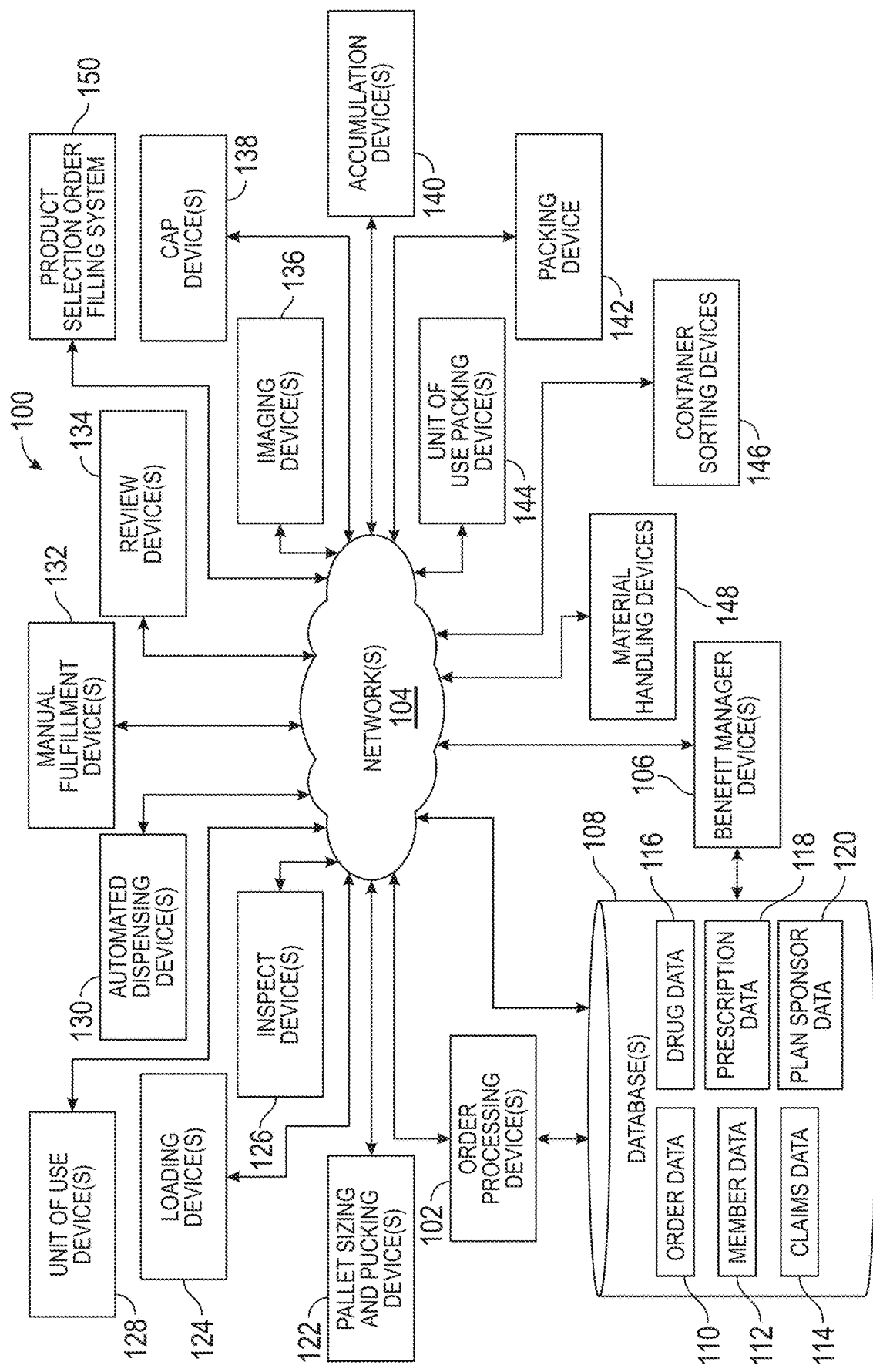
FIG. 1 illustrates, by way of example and not limitation, a block diagram of an embodiment of a pharmacy order processing system.

FIG. 1 illustrates, by way of example and not limitation, a block diagram of an embodiment of a pharmacy order processing system. While the system 100 is generally described as being deployed in a high-volume fulfillment center (e.g., a mail order pharmacy, a direct delivery pharmacy, a home delivery pharmacy and the like), the system 100 and/or components thereof may otherwise be deployed. The system 100 may include an order processing device 102 configured to communicate over a network 104 with a benefit manager device 106. Additional devices which may communicate over the network 104 with the benefit manager device 106 and/or the order processing device 102 may include at least some of: database(s) 108 which may store one or more than one of order data 110, member data 112, claims data 114, drug data 116, prescription data 118, and plan sponsor data 120; pallet sizing and pucking device(s) 122 (or other cart-like devices used to transport product); loading device(s) 124; inspect device(s) 126; unit-of-use device(s) 128; automated dispensing device(s) 130; manual fulfillment device(s) 132; review device(s) 134; imaging device(s) 136; cap device(s) 138; accumulation device(s) 140; packing device(s) 142; unit-of-use packing device(s) 144, container sorting device(s) 146 configured to image and sort containers, material handlings devices 148 configured to transport the containers throughout the system 100, and a product selection order filling system 150 configured to fill daily dosage unit pharmacy orders. The system 100 may also include additional devices.

The order processing device 102 may receive information about prescriptions being filled at a pharmacy in which the order processing device 102 is deployed. In general, the order processing device 102 may be a device located within or otherwise associated with a pharmacy location to enable fulfillment of a prescription by dispensing prescription drugs. In some embodiments, the order processing device 102 may be a device separate from a pharmacy that enables communication with other devices located within a pharmacy. For example, the order processing device 102 may be in communication with another order processing device 102 and/or other devices, such as other devices illustrated in FIG. 1, located with a pharmacy. In some embodiments, an external pharmacy order processing device 102 may have limited functionality (e.g., as operated by a patient requesting fulfillment of a prescription drug) when an internal pharmacy order processing device 102 may have greater functionality (e.g., as operated by a pharmacy).

The order processing device 102 may track a pharmaceutical order as it is fulfilled. A pharmaceutical order may include a prescription order for prescription medicine as well as may include non-prescription medicine and/or non-medical products. A prescription order may include one or more than one prescription to be filled by the pharmacy. The order processing device 102 may make pharmacy routing decisions and/or order consolidation decisions for a prescription order. The pharmacy routing decisions may include what device or devices in the pharmacy are responsible for filling at least a portion of the pharmaceutical order, where the order consolidation decisions include whether portions of a pharmaceutical order or multiple pharmaceutical orders should be shipped together for a patient or a patient family. The order processing device 102 may operate in combination with the benefit manager device 106.

Examples of the order processing device 102 may include a set-top box (STB), a receiver card, a mobile telephone, a personal digital assistant (PDA), a display device, a portable gaming unit, a tablet, and a computing system; however other devices may also be used. For example, the order processing device 102 may include a mobile electronic device, such an iPhone or iPad device by Apple, Inc., mobile electronic devices powered by ANDROID by Google, Inc., and a BLACKBERRY device by Blackberry Limited. The order processing device 102 may include other computing devices, such as desktop computing devices, notebook computing devices, netbook computing devices, gaming devices, and the like. The device 102 may include a processor, a memory to store data and instructions, and communication functionality. Other types of electronic devices that can use rules and instructions to execute various functions may also be used.

Examples of the network 104 include Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. The network 104 may include optical communications. The network 104 may be a local area network or a global communication network, such as the Internet. Other conventional and/or later developed wired and wireless networks may also be used. In some embodiments, the network 104 may include a prescribing network such as the electronic prescribing network operated by Surescripts of Arlington, Va.

The benefit manager device 106 may be operated by an entity at least partially responsible for creation and/or management of the pharmacy or drug benefit. The benefit manager operating the benefit manager device 106 may be a pharmacy benefit manager (PBM), or may be other entities that operate the benefit manager device 106 either on behalf of themselves, the PBM, or another entity. For example, the benefit manager may be operated by a health plan, a retail pharmacy chain, a drug wholesaler, a data analytics or other type of software-related company, or the like. In some embodiments, a PBM that provides the pharmacy benefit may also provide one or more than one additional benefits including a health benefit, a dental benefit, a vision benefit, a wellness benefit, a radiology benefit, a pet care benefit, an insurance benefit, a long term care benefit, a nursing home benefit, and the like. The PBM may, in addition to its PBM operations, operate one or more than one pharmacy. The pharmacies may be retail pharmacies, mail order pharmacies, etc.

By way of example and not limitation, a member (or a person on behalf of the member) of a pharmacy benefit plan administered by or through the PBM may attempt to obtain a prescription drug at a retail pharmacy location where the member can obtain drugs in a physical store from a pharmacist or pharmacist technician, or in some instances through mail order drug delivery from a mail order pharmacy location. The member may obtain a prescription drug directly or indirectly through the use of a machine, such as a kiosk, vending unit, mobile electronic device, or a different type of mechanical, electrical, an electronic communication device and/or computing device.

The member may have a co-pay for the prescription drug that reflects an amount of money that the member is responsible to pay the pharmacy for the prescription drug. The money paid by the member to the pharmacy may come from the personal funds of the member, a health savings account (HSA) of the member or the member's family, a health reimbursement arrangement (HRA) of the member or the member's family, a flexible spending accounts (FSA) of the member or the member's family, or the like. An employer of the member may directly or indirectly fund or reimburse the member or an account of the member for the co-pay. The amount of the co-pay paid by the member may vary by the benefit plan of a plan sponsor or client with the PBM. The member's co-pay may be based on a flat co-pay (e.g., $10), co-insurance (e.g., 10%), and/or a deductible (e.g., for first $500 of annual prescription drug spend) for certain prescription drugs, certain types of prescription drugs, and/or all prescription drugs. In certain instances, the member may not pay the co-pay or may only pay for a portion of a co-pay for a prescription drug. For example, if the usual and customary cost for a generic version of a prescription drug is $4, and the member's flat co-pay is $20 for the prescription drug, the member may only pay $4 to receive the prescription drug. In another example involving a worker's compensation claim, no co-pay may be due by the member for the prescription drug. The co-pay may also vary based on the channel used to receive the prescription drug. For example, the co-pay for receiving prescription drugs from a mail order pharmacy location may be less than the co-pay for receiving prescription drugs from a retail pharmacy location.

In conjunction with receiving the co-pay (if any) from the member and dispensing the prescription drug to the member, the pharmacy submits a claim to the PBM for the prescription drug. The PBM may perform certain adjudication operations including verifying the eligibility of the member, reviewing the formulary of the member to determine appropriate co-pay, coinsurance, and deductible for the prescription drug, and performing a drug utilization review (DUR) on the member. The PBM then provides a response to the pharmacy following performance of at least some of the aforementioned operations. As part of the adjudication, the plan sponsor (or the PBM on behalf of the plan sponsor) ultimately reimburses the pharmacy for filling the prescription drug when the prescription drug was successfully adjudicated. The aforementioned adjudication operations generally occur before the co-pay is received and the prescription drug dispensed. However, the operations may occur simultaneously, substantially simultaneously, or in a different order. In addition, more or less adjudication operations may be performed as at least part of the adjudication process.

The amount of reimbursement paid to the pharmacy by a plan sponsor and/or money paid by the member may be based at least in part on the type of pharmacy network in which the pharmacy is included. Other factors may be used to determine the amount in addition to the type of pharmacy network. For example, if the member pays the pharmacy for the prescription without using the prescription drug benefit provided by the benefit manager, the amount of money paid by the member may be higher and the amount of money received by the pharmacy for dispensing the prescription drug and for the prescription drug itself may be higher. Some or all of the foregoing operations may be performed by executing instructions on the benefit manager device 106 and/or an additional device.

In some embodiments, at least some of the functionality of the order processing device 102 may be included in the benefit manager device 106. The order processing device 102 may be in a client-server relationship with the benefit manager device 106, a peer-to-peer relationship with the benefit manager device 106, or in a different type of relationship with the benefit manager device 106.

The order processing device 102 and/or the benefit manager device 106 may be in communication directly (e.g., through local storage) and/or through the network 104 (e.g., in a cloud configuration or software as a service) with a database 108 (e.g., as may be retained in memory or otherwise). The database 108 may store order data 110, member data 112, claims data 114, drug data 116, prescription data 118, and/or plan sponsor data 120. Other data may be stored in the database 108.

The order data 110 may include data related to the order of prescriptions including the type (e.g., drug name and strength) and quantity of each prescription in a prescription order. The order data 110 may also include data used for completion of the prescription, such as prescription materials. Prescription materials may be a type of order materials that include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, or the like. The order data 110 may be used by a high-volume fulfillment center to fulfill a pharmacy order.

In some embodiments, the order data 110 may include verification information associated with fulfillment of the prescription in the pharmacy. For example, the order data 110 may include videos and/or images taken of: the prescription drug prior to dispensing, during dispensing, and/or after dispensing; a prescription container (e.g., a prescription bottle and sealing lid) used to contain the prescription drug prior to dispensing, during dispensing, and/or after dispensing; the packaging and/or packaging materials used to ship or otherwise deliver the prescription drug prior to dispensing, during dispensing, and/or after dispensing; and/or the fulfillment process within the pharmacy. Other type of verification information such as bar code data read from pallets used to transport prescriptions within the pharmacy may also be stored as order data 110.

The member data 112 includes information regarding the members associated with the benefit manager. Examples of the member data 112 include name, address, telephone number, e-mail address, prescription drug history, and the like. The member data 112 may include a plan sponsor identifier that identifies the plan sponsor associated with the member and/or a member identifier that identifies the member to the plan sponsor. The member data 112 may include a member identifier that identifies the plan sponsor associated with the patient and/or a patient identifier that identifies the patient to the plan sponsor. The member data 112 may also include, by way of example, dispensation preferences such as type of label, type of cap, message preferences, language preferences, or the like.

The member data 112 may be accessed by various devices in the pharmacy, e.g., the high-volume fulfillment center, to obtain information utilized for fulfillment and shipping of prescription orders. In some embodiments, an external order processing device 102 operated by or on behalf of a member may have access to at least a portion of the member data 112 for review, verification, or other purposes.

In some embodiments, the member data 112 may include information for persons who are patients of the pharmacy but are not members in a benefit plan being provided by the benefit manager. For example, these patients may obtain drug directly from the pharmacy, through a private label service offered by the pharmacy, the high-volume fulfillment center, or otherwise. In general, the use of the terms member and patient may be used interchangeably herein.

The claims data 114 includes information regarding pharmacy claims adjudicated by the PBM under a drug benefit program provided by the PBM for one, or more than one, plan sponsors. In general, the claims data 114 includes an identification of the client that sponsors the drug benefit program under which the claim is made, and/or the member that purchased the prescription drug giving rise to the claim, the prescription drug that was filled by the pharmacy (e.g., the national drug code number), the dispensing date, generic indicator, GPI number, medication class, the cost of the prescription drug provided under the drug benefit program, the copay/coinsurance amount, rebate information, and/or member eligibility. Additional information may be included.

In some embodiments, other types of claims beyond prescription drug claims may be stored in the claims data 114. For example, medical claims, dental claims, wellness claims, or other type of health care-related claims for members may be stored as a portion of the claims data 114.

In some embodiments, the claims data 114 includes claims that identify the members with whom the claims are associated. In some embodiments, the claims data 114 includes claims that have been de-identified (e.g., associated with a unique identifier but not with a particular, identifiable member).

The drug data 116 may include drug name (e.g., technical name and/or common name), other names by which the drug is known by, active ingredients, an image of the drug (e.g., in pill form), and the like. The drug data 116 may include information associated with a single medication or multiple medications.

The prescription data 118 may include information regarding prescriptions that may be issued by prescribers on behalf of patients, who may be members of the drug benefit plan, for example to be filled by a pharmacy. Examples of the prescription data 118 include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.).

In some embodiments, the order data 110 may be linked to associated member data 112, claims data 114, drug data 116, and/or prescription data 118.

The plan sponsor data 120 includes information regarding the plan sponsors of the benefit manager. Examples of the plan sponsor data 120 include company name, company address, contact name, contact telephone number, contact e-mail address, and the like.

The order processing device 102 may direct at least some of the operations of the devices illustrated in FIG. 1. In some embodiments, operations performed by one of these devices may be performed sequentially, or in parallel with the operations of another device as may be coordinated by the order processing device 102. In some embodiments, the order processing device 102 tracks a prescription with the pharmacy based on operations performed by one or more of the devices illustrated in FIG. 1.

A material transport system or assembly may be used to transport product. For example, conveyors may include gravity conveyors or powered conveyors. Powered conveyors may include but are not limited chain-driven conveyors, pallet conveyors and servo-controlled conveyors. Intelligent conveyor systems may be designed to control the speed and/or direction of lines of article motion, and may allow individual articles to be inserted or removed from the line. Intelligent conveyor system may be designed to enable electronic movement control of individual transport mechanisms (e.g. pucks) for the product. For example, conveyor systems may be designed with one or more servo motors, controlled by a programmable servo controller, to electronically control movement of an individual puck. An example of an intelligent system may move individual carts, with or without a puck in or otherwise connected to the cart, along rails, under electronic control, in order to enable individual articles to be inserted and/or removed from line(s) of articles. Material transport systems may include a rotating structure with a periphery. Objects may be on a surface near the periphery such that they move as the structure rotates. Other material transport systems may be used. The material transport system may include combinations different types of material transport systems, such as a combination of two or more of a gravity conveyor, a power conveyor, and an intelligent conveyor.

In some embodiments, by way of example, the system 100 may transport product such as prescription drug containers (e.g., between or among devices, such as one of more devices illustrated in FIG. 1, in the high-volume fulfillment center) by use of pallets. The pallet sizing and pucking device 122 may configure pucks in a pallet. A pallet may be a transport structure for a number of the prescription containers 101, and may include a number of cavities. A puck may be placed in one or more than one of the cavities in a pallet by the pallet sizing and pucking device 122. A puck may include a receptacle sized and shaped to receive a prescription container 101. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 102 based on prescriptions which the order processing device 102 decides to launch. In general, prescription orders in the storage device 108 reside in one or more than one queues, and are generally launched in a first-in-first-out order. However, the order processing device 102 may use logic and a variety of factors to determine when and how prescriptions are to be launched. For example, some non-limiting factors which may alter the first-in-first-out order of launching prescriptions in a pharmacy include the age of the order, whether the order required an outreach to a physician or some other intervention, whether there are any performance guarantees with plan sponsors or members, the available inventory of a given pharmaceutical in view of existing prescriptions already launched which will require that pharmaceutical, the zip code to which the order will be shipped, the workload and volume of various parts of the pharmacy, whether valid paperwork for the order has been received, and/or similar orders for the same pharmaceutical that are already to be launched. The logic may be implemented directly in the pallet sizing and pucking device 122, in the order processing device 102, in both devices 102, 122, or otherwise. Once a prescription is set to be launched, a puck suitable for the appropriate size of container for that prescription may be positioned in a pallet by a robotic arm or pickers. The pallet sizing and pucking device 122 may launch a pallet once pucks have been configured in the pallet.

The loading device 124 may load prescription containers into the pucks on a pallet by a robotic arm, pick and place mechanism, or the like. In one embodiment, the loading device 108 has robotic arms or pickers to grasp a prescription container and move it to and from a pallet or a puck. The loading device 124 may also print a label which is appropriate for a container that is to be loaded onto the pallet, and apply the label to the container 101. The pallet may be located on a conveyor assembly during these operations, e.g., at the high-volume fulfillment center.

The inspect device 126 may verify that containers are correctly labeled and positioned on a material transport system. For example, the inspect device 126 may verify that containers in a pallet are in correct spots on the pallet. The inspect device 126 may scan the label on one or more than one container on the pallet. Labels of the containers may be scanned or imaged in full or in part by the inspect device 126. Such imaging may occur after the container has been lifted out of its puck by a robotic arm, picker, or the like, or may be otherwise scanned or imaged while retained in the puck. In some embodiments, images and/or video captured by the inspect device 126 may be stored in the database 108 as order data 110.

The unit-of-use device 128 may temporarily store, monitor, label and/or dispense unit-of-use products. In general, unit-of-use products are prescription drug products that may be delivered to a patient or member without being repackaged at the pharmacy. These products may include pills in a container 101, pills in a blister pack, inhalers, and the like. Prescription drug products dispensed by the unit-of-use device 128 in their original packaging may be packaged individually or collectively for shipping, or may be shipped in combination with other prescription drugs dispenses by other devices in the high-volume fulfillment center.

The automated dispensing device 130 may include one or more than one device that dispense prescription drugs or pharmaceuticals into prescription containers in accordance with one or multiple prescription orders. In general, the automated dispensing device 130 may include mechanical and electronic components with, in some embodiments, software and/or logic to facilitate pharmaceutical dispensing that would otherwise be performed in a manual fashion by a pharmacist and/or pharmacist technician. For example, the automated dispensing device 130 may include high-volume fillers that fill a number of prescription drug types at a rapid rate and blister pack machines that dispense and pack drugs into a blister pack. Prescription drugs dispensed by the automated dispensing devices 130 may be packaged individually or collectively for shipping, or may be shipped in combination with other prescription drugs dispenses by other devices in the high-volume fulfillment center.

The manual fulfillment device 132 may provide for manually fulfillment of prescriptions. For example, the manual fulfillment device 132 may receive or obtain a container and enable fulfillment of the container by a pharmacist or pharmacy technician. In some embodiments, the manual fulfillment device 132 provides the filled container to another device in the system 100 to be joined with other containers in a prescription order for a patient or member. In general, a manual fulfillment may include operations at least partially performed by a pharmacist or pharmacy technician. For example, a person may retrieve a supply of the prescribed drug, may make an observation, may count out a prescribed quantity of drugs and place them into a prescription container 101, or the like. Some portions of the manual fulfillment process may be automated by use of a machine. For example, counting of capsules, tablets, or pills (types of drug delivery structures) may be at least partially automated (e.g., through use of a pill counter). Prescription drugs dispensed by the manual fulfillment device 132 may be packaged individually or collectively for shipping, or may be shipped in combination with other prescription drugs dispenses by other devices in the high-volume fulfillment center.

The review device 134 may process prescription containers to be reviewed by a pharmacist for proper pill count, exception handling, prescription verification, and the like. Fulfilled prescriptions may be manually reviewed and/or verified by a pharmacist, as may be required by state or local law. A pharmacist or other licensed pharmacy person who may dispense certain drugs in compliance with local and/or other laws may operate the review device 134 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been cancelled, containers with defects, and the like.

The imaging device 136 may image containers once they have been filled with pharmaceuticals. The imaging device 136 may measure the fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 102, and/or stored in the database 110 as part of the order data 110.

The cap device 138 may be used to cap or otherwise seal a prescription container 101. In some embodiments, the cap device 138 may secure a prescription container with a type of cap in accordance with a patient preference (e.g., a preference regarding child resistance), a plan sponsor preference, a prescriber preference, or the like. The cap device 138 may also etch a message into the cap, although this process may be performed by a subsequent device in the high-volume fulfillment center. The cap may include an induction liner. After the cap with the induction liner is placed on the container, an induction sealer may heat the induction liner such that the induction liner forms a tamper-evident seal over the container.

The accumulation device 140 may be used to accumulate containers, including one or more types of containers, of prescription drugs in a prescription order. The accumulation device 140 may accumulate prescription containers from various devices or areas of the pharmacy. For example, the accumulation device 140 may accumulate prescription containers from the unit-of-use device 128, the automated dispensing device 130, the manual fulfillment device 132, and the review device 134, at the high-volume fulfillment center. The accumulation device 140 may be used to group the prescription containers prior to shipment to the member or otherwise.

The packing device 142 may be configured to package a prescription order in preparation for shipping the order. For example, the packing device 142 may box, bag, or otherwise package the fulfilled prescription order for delivery. The packing device 142 may further place inserts into the packaging. For example, bulk prescription orders may be shipped in a box, while other prescription orders may be shipped in a bag which may be a wrap seal bag. The packing device 142 may label the box or bag with the address and a recipient's name. The packing device 142 may sort the box or bag for mailing in an efficient manner (e.g., sort by delivery address). The packing device 142 may include ice or temperature sensitive elements for prescriptions which are to be kept within a temperature range during shipping in order to retain efficacy or otherwise. The package may then be shipped through postal mail, through a mail order delivery service that ships via group and/or air (e.g., UPS, FedEx, or DHL), through delivery service, through a locker box at a shipping site (e.g., Amazon locker or a PO Box), or otherwise.

The unit-of-use packing device 144 may be configured to package a unit-of-use prescription order in preparation for shipping the order. The unit-of-use packing device 144 may include manual scanning of containers to be bagged for shipping to verify each container in the order.

The devices illustrated in FIG. 1 may be separate device or combined. When multiple devices are present, the multiple devices may be of the same device type or models or may be a different device type or model.

Moreover, the system 100 shows a single network 104; however, multiple networks can be used. The multiple networks may communicate in series with each other to link the devices or in parallel to link the devices. Multiple devices may share processing and/or memory resources. The devices may be located in the same area or in different locations. For example, the devices may be located in a building or set of adjoining buildings. They may be interconnected (e.g. by conveyors), networked, and/or otherwise in contact with one another or integrated with one another, e.g., at the high-volume fulfillment center. In addition, the functionality of a device may be split among a number of discrete devices and/or combined with other devices.

Figure 2:
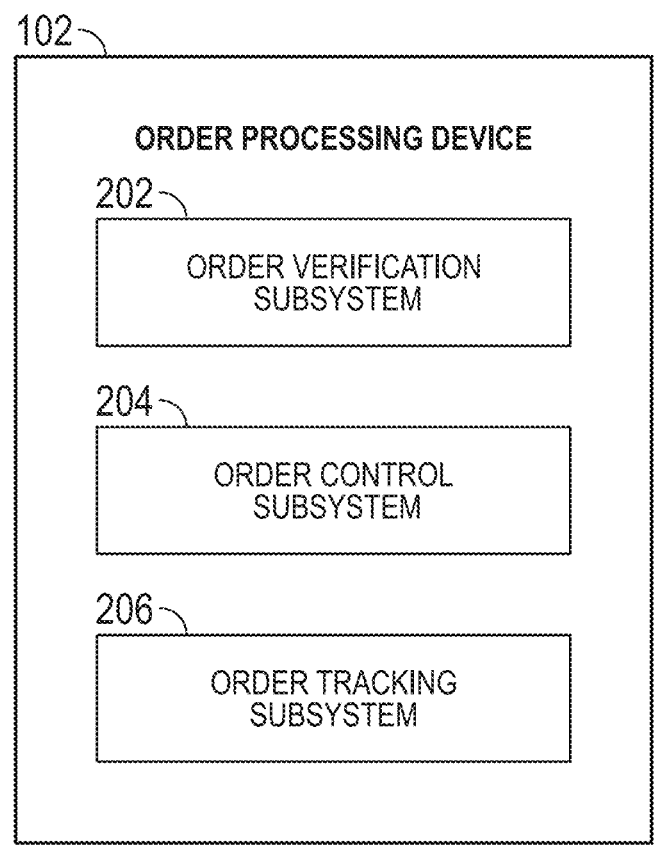
FIG. 2 illustrates, by way of example and not limitation, a block diagram of an embodiment of an order processing device that may be deployed within an order processing system such as the system of FIG. 1.

FIG. 2 illustrates, by way of example and not limitation, a block diagram of an embodiment of an order processing device that may be deployed within an order processing system such as the system of FIG. 1. The order processing device 102 may be used by one or more than one operator to generate pharmaceutical orders (e.g. prescription orders), make routing decisions, make order consolidation decisions, and/or view order status and other order related information. For example, the pharmaceutical order may be comprised of order components. The order processing device 102 may receive instructions to fulfill an order without operator intervention. An order component may include a prescription drug fulfilled by use of a container through the system 100. The order processing device 102 may direct an order component to the manual fulfillment device 132 and/or to the review device 134, and direct other components to the automated dispensing device 130. The order processing device 102 may direct the filling of an order component to be filled by the product selection order filling system 150. The order processing device 102 may direct order components to the accumulation device 140 for aggregation before shipping. The order processing device 102 may direct the order components directly to the packing device 142 if the prescription order does not require accumulation from various areas of the pharmacy for completion. The order processing device 102 may be deployed in the system 100, or may otherwise be used.

The order processing device 102 may include an order verification subsystem 202, an order control subsystem 204, and/or an order tracking subsystem 206. Other subsystems may also be included in the order processing device 102.

The order verification subsystem 202 may communicate with the benefit manager device 106 to, verify the eligibility of the member, review the formulary to determine appropriate co-pay, coinsurance, and deductible for the prescription drug, and/or perform a DUR. Other communications between the order verification subsystem 202 and the benefit manager device 106 may be performed for a variety of purposes.

The order control subsystem 204 controls various movements of the containers and/or pallets along with various filling functions during their progression through the system 100. The order control subsystem 204 may control filling of a plurality of individual doses for dosing events by the product selection order filling system 150. In some embodiments, the order control subsystem 204 may identify a prescribed drug in one or more than one prescription order as capable of being fulfilled by the automated dispensing device 130 or the automated per dosing event system 150. The order control subsystem 204 may determine which prescriptions are to be launched, and may determine that a pallet of automated-fill containers is to be launched. The order control subsystem 204 may determine that an automated-fill prescription of a specific pharmaceutical is to be launched, and may examine a queue of orders awaiting fulfillment for other prescription orders which will be filled with the same pharmaceutical. The order control subsystem 204 may then launch orders with similar automated-fill pharmaceutical needs together in a pallet to the automated dispensing device 130. As the devices may be interconnected by a system of one or more conveyors or other container movement systems, the order control subsystem 204 may control various conveyors to deliver the pallet from the loading device 124 to the manual fulfillment device 132, for example.

The order tracking subsystem 206 may track a prescription order as it progresses through (or stops at) various stations toward fulfillment. The order tracking subsystem 206 may track, record and/or update order history, order status or the like, e.g., the prescriptions filled by the system 150 and the automated dispensing devices 130. The order tracking subsystem 206 may store data locally (e.g., in a memory) or as a portion of the order data 110 stored in the storage device 108.

The order processing device 102 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The order processing device 102 may be utilized by the pharmacy to submit the claim to the PBM for adjudication.

Additionally, in some embodiments, the order processing device 102 may enable information exchange between the pharmacy and the PBM, for example, to allow the sharing of member information such as drug history, and the like, that may allow the pharmacy to better service a member (e.g., by providing more informed therapy consultation and drug interaction information, etc.). In some embodiments, the benefit manager device 106 may track prescription drug fulfillment and/or other information for patients that are not members or have not identified themselves as members, at the time (or in conjunction with the time) in which they seek to have a prescription filled at a pharmacy.

The order processing device 102 may also track and/or schedule literature or paperwork associated with each prescription order or multiple prescription orders that are being shipped together. The literature being tracked can be associated with a dosing event delivery from system 150 or the automated dispensing device 130.

The order processing device 102 may include circuitry, a processor, a memory to store data and instructions, and communication functionality. The order processing device 102 is dedicated to performing processes, methods and/or instructions described herein. Other types of electronic devices specifically configured to implement with the processes, methods and/or instructions described herein may also be used.

The storage device 108 may include: a non-transitory storage (e.g., memory, hard disk, CD-ROM, etc.) in communication with the benefit manager device 106, and/or the order processing device 102 directly and/or over the network 104. The non-transitory storage may store order data 110, member data 112, claims data 114, drug data 116, prescription data 118, and/or plan sponsor data 120. Further, the pharmacy order processing system 100 includes additional devices, including at least one container disassembly workstation 125, tray delivery conveyors 124, picking workstations 126, inspection workstations 130, packing delivery conveyors 132, packing workstations 134, and shipping conveyors 136, each additional device able to communicate with each other directly or over the network 104.

Figure 3:
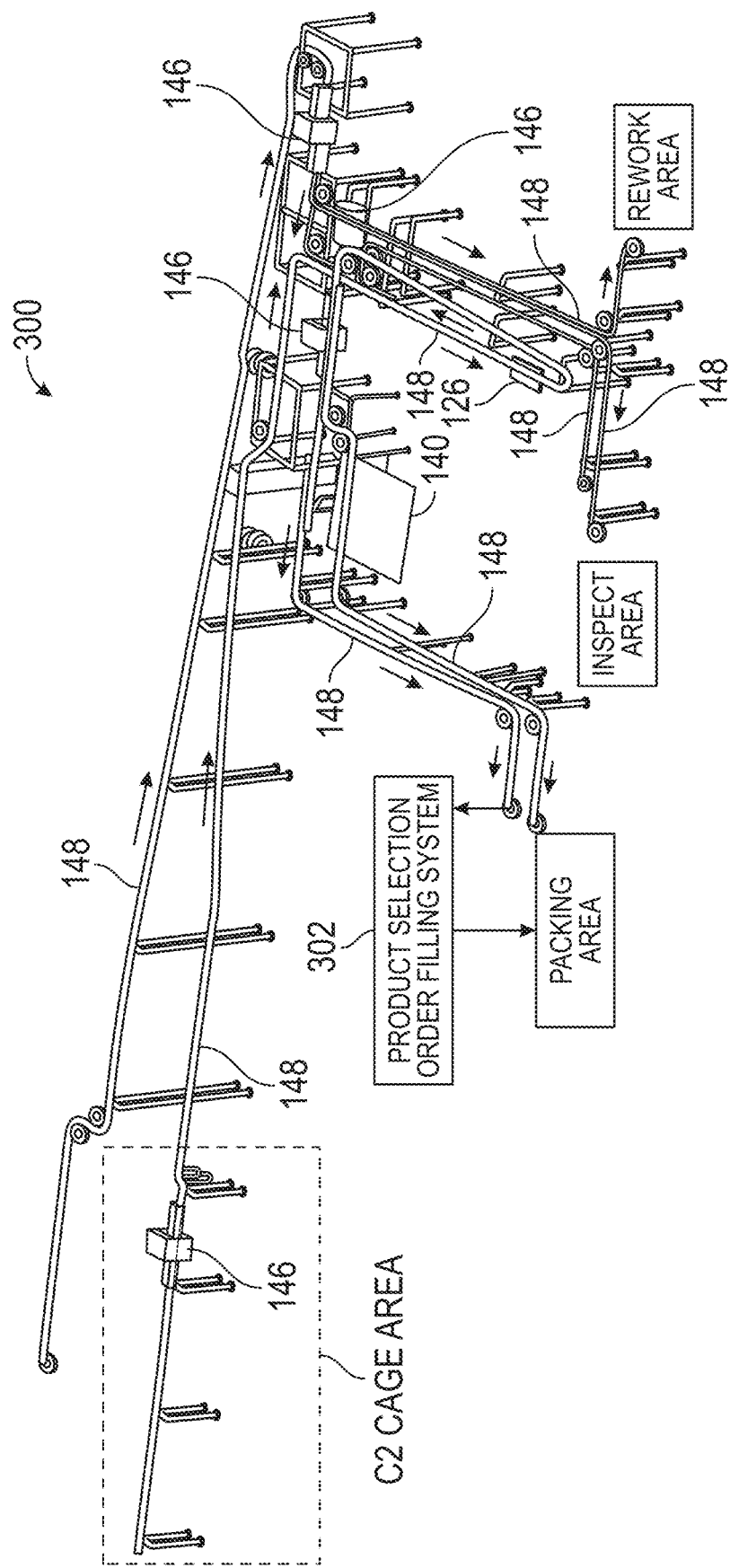
FIG. 3 illustrates, by way of example and not limitation, an embodiment of a product selection order filling system that may be deployed within a pharmacy order processing system such as the system of FIG. 1.

FIG. 3 illustrates, by way of example and not limitation, an embodiment of a product selection order filling system that may be deployed within a pharmacy order processing system such as the system of FIG. 1. The figure illustrates a "controls cage". In this embodiment, the controls cage is a more restricted or controlled-access portion of the pharmacy order processing system 100 separate from other portions of the pharmacy order processing system 100. The controls cage and be a separate room with a conveyor extending from the room. The controls cage can be metal or polymer enclosure surrounding a portion of the conveyor and other device to restrict access to the caged volume. The controls cage is adapted to rapidly process, at least a portion of pharmacy orders that include controlled substances having a C2, C3, C4, or C5 classification, in at least some cases from receipt of an order to shipping a packed filled order. In this embodiment, the controls cage is separate from the non-controlled substance portion of the pharmacy order processing system 100 and includes a separate C2 cage area for processing C2 substances. In other embodiments, the controls cage is substantially continuous with the non-controlled substance portion of the pharmacy order processing system 100.

In the example embodiment, the portion 300 of the pharmacy order processing system 100 illustrated in FIG. 3 includes an example product selection order filling system 302, an accumulation device 140, an inspect device 126, four container sorting devices 146, a packing device 142, and multiple material handling devices 148 extending between at least one of the accumulation device 140, the inspect device 126, the container sorting devices 146, the packing device 142, a packing area, an inspect area, and a rework area. In this embodiment, the inspect device 126 is a scale configured to weigh the containers 101. In other embodiments, the controls cage includes any number of the order filling systems, the accumulation devices 140, the inspect devices 126, the container sorting devices 146, the packing device 142, and the material handling devices 148 arranged in any configuration that facilitates operation of the pharmacy order processing system 100 as described herein.

Figure 4:
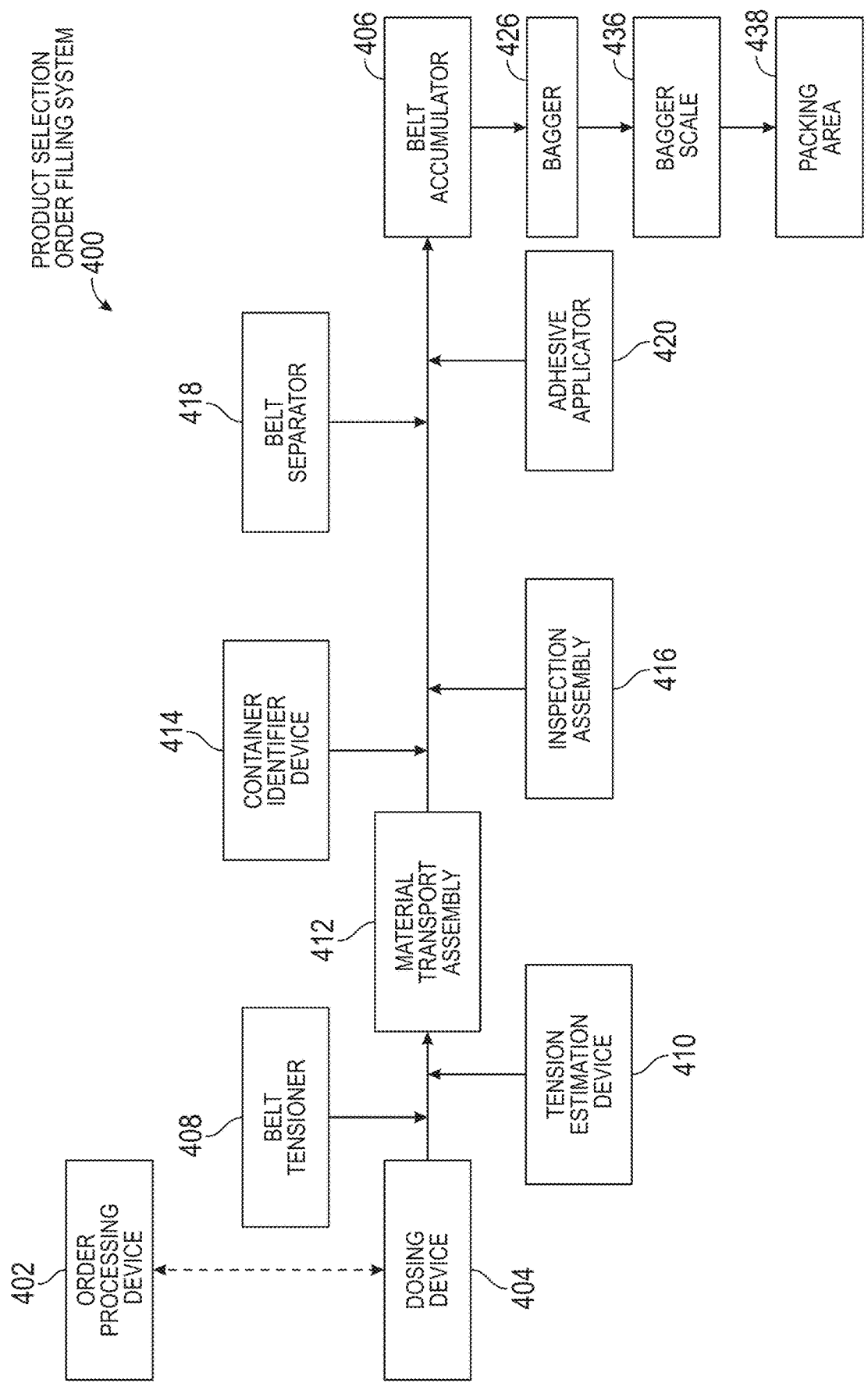
FIG. 4 illustrates, by way of example and not limitation, a block diagram of a product selection order filling system that may be deployed within a pharmacy order processing system such as the system of FIG. 1.
Figure 5:
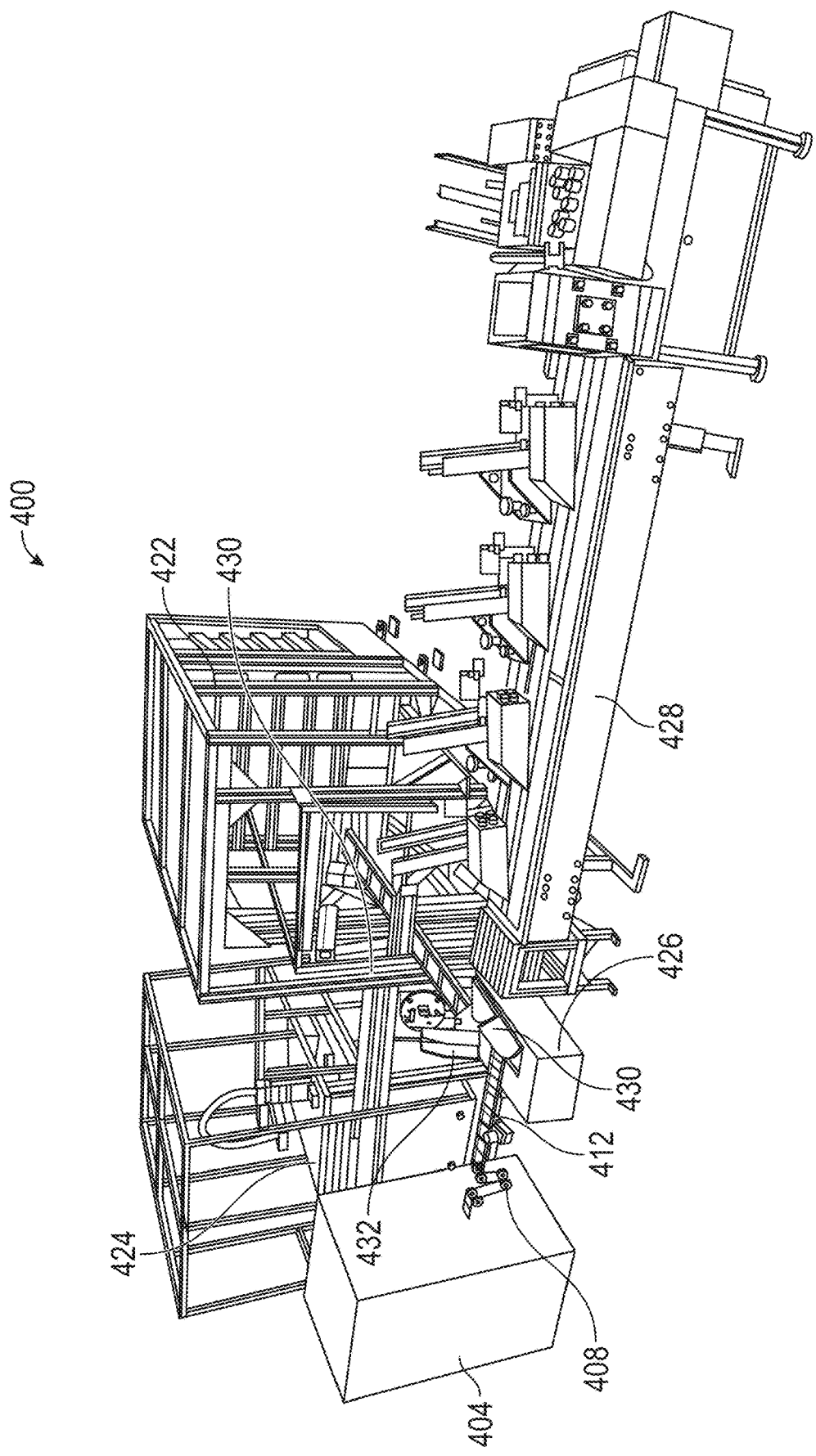
FIG. 5 illustrates, by way of example and not limitation, a perspective view of an embodiment of the product selection order filling system shown in FIG. 4.
Figure 6A:
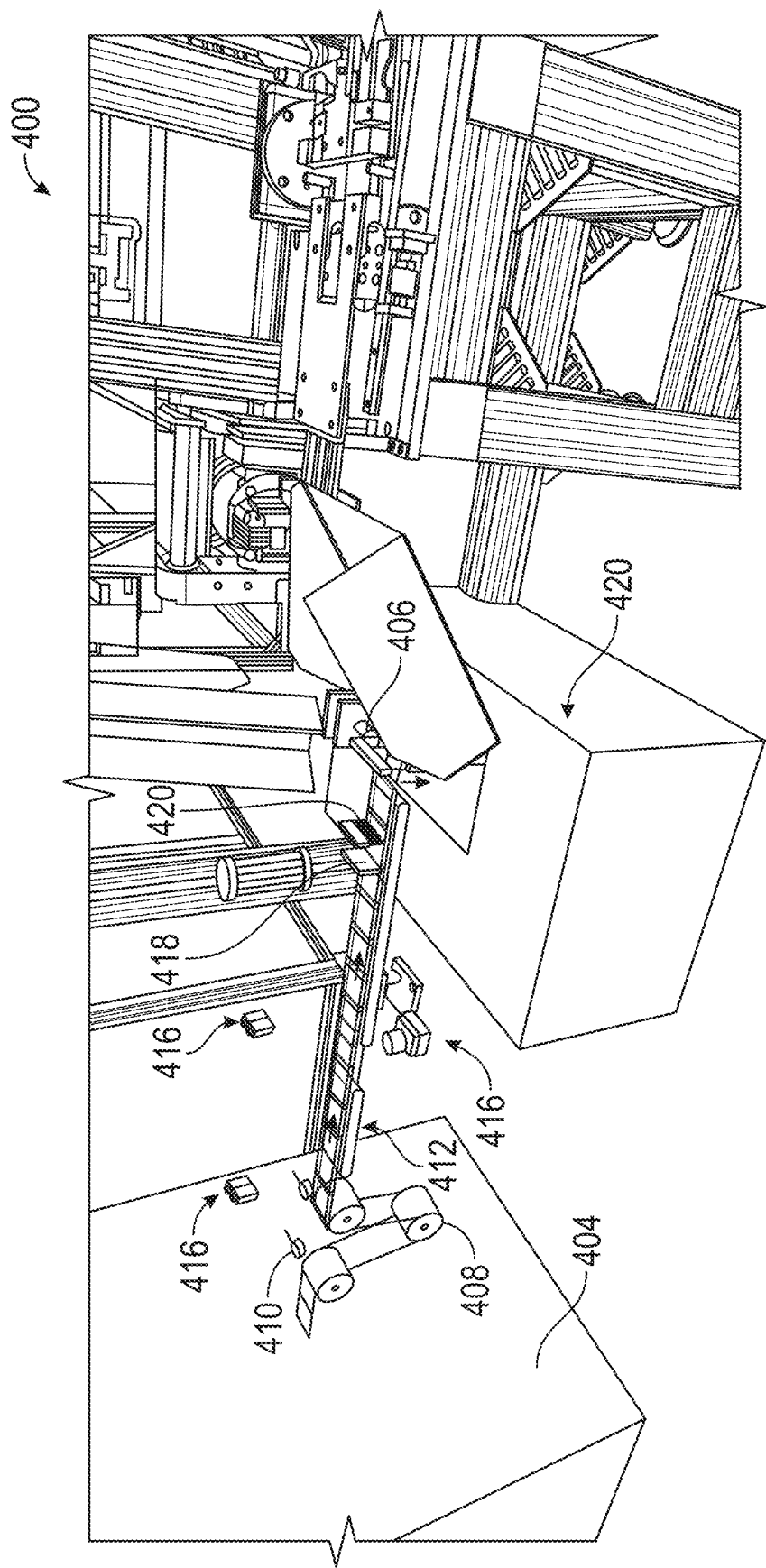
Figure 6B:
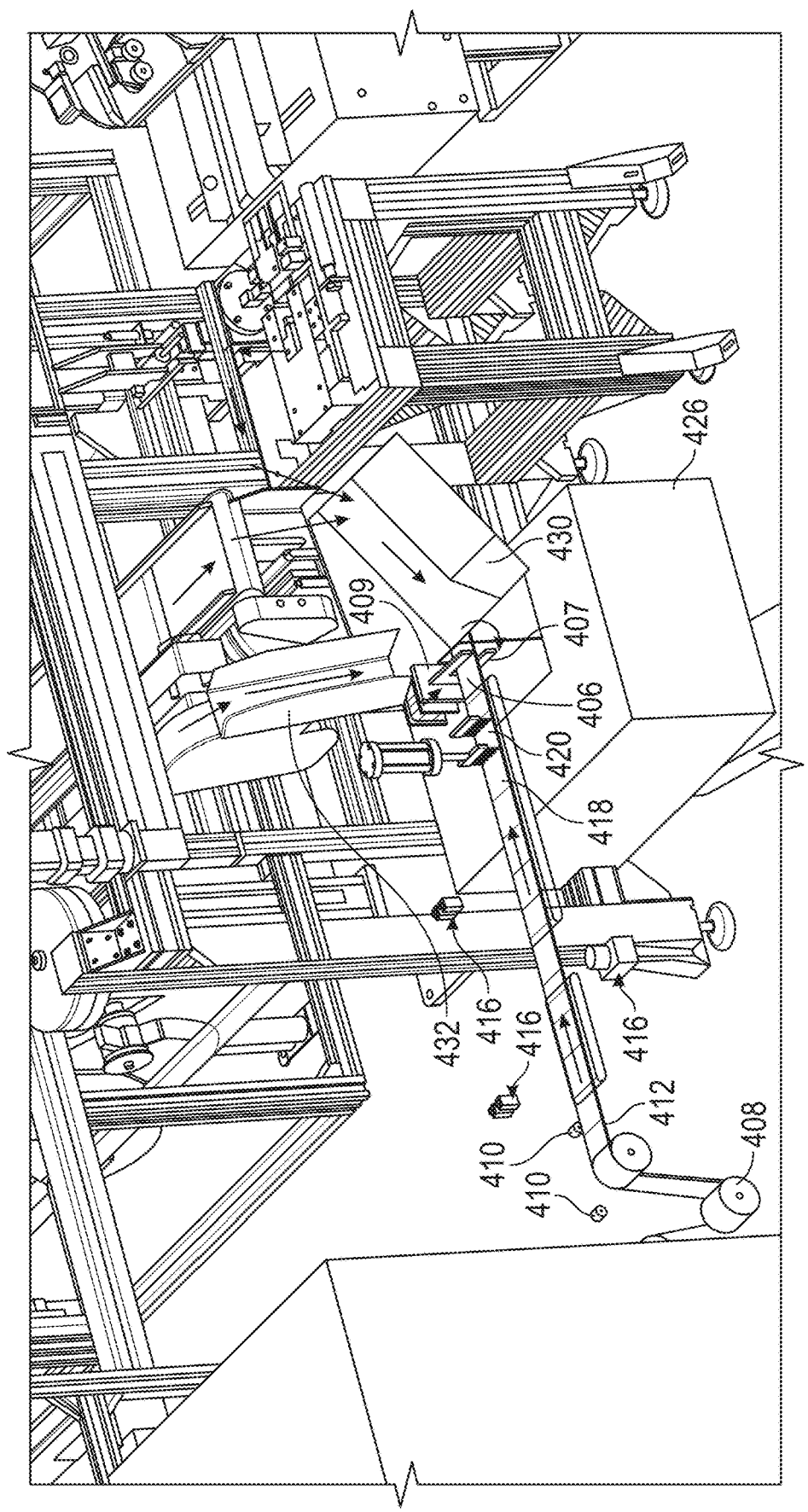

FIGS. 4, 5 and 6A-6C are diagrams of an example product selection order filling system 400 that may be deployed within the system 100 of FIG. 1, or may otherwise be deployed. FIG. 4 illustrates, by way of example and not limitation, a block diagram of a product selection order filling system that may be deployed within a pharmacy order processing system such as the system of FIG. 1, while FIGS. 5 and 6A-6C reflect perspective views of the product selection order filling system 400.

In an embodiment, the product selection order filling system 400 includes an order processing device 402, a dosing device 404, a belt accumulator 406, a belt tensioner 408, a tension estimation device 410, a material transport assembly 412, a container identifier device 414, an inspection assembly 416, a belt separator 418, an adhesive applicator 420, a box unit-of-use device 422, a bottle accumulator 424, a bagger 426, a folded paper/envelope feeder device 428, a folded paper/pick and place device 430, a bottle chute 432, a unit-of-use chute 434, a bagger scale 436, and a bagging area 438. The product selection order filling system 400 can be included in any portion of the pharmacy order processing system 100 that facilitates operation of the pharmacy order processing system 100 as described herein.

In an example embodiment, the order processing device 402 may be configured to receive orders for product selections and to communicate with the dosing device 404 that is connected to the order processing device 402. For example, the order processing device may be configured to receive pharmaceutical orders including orders for drugs used in multi-drug regimens, respectively, where each of the multi-drug regimens has a plurality of scheduled dosing events. In some embodiments, the order processing device 102 includes the functionality of order processing device 402.

The dosing device 404 may be configured to dispense selections, or daily dosing units, of products into multiple packets as part of the daily dosage unit pharmacy order. The dosing device may be a drug packet dispensing device configured to communicate with the order processing device and dispense drug packets based on the received pharmaceutical orders. In some embodiments, the dosing device 404 may be configured to dispense selections of products into any other type of container that facilitates operation of the product selection order filling system 400 as described herein. The drug packets may be dispensed as a belt of drug packets in which adjacent drug packets in the belt are connected, where each of the drug packets may correspond to one of the plurality of scheduled dosing events and each of the drug packets may contain one or more of the drugs used in the multi-drug regimen for one of the plurality of scheduled dosing events. Each of the drug packets may have a machine-readable identifier identifying each of the drug packets dispensed from the drug packet dispensing device. Examples of machine-readable identifiers include, but are not limited to, bar codes, Quick Response (QR) codes, Radio Frequency Identification (RFID), Optical Character Recognition (OCR), and the like. The packets may be formed from continuous material including multiple perforations defining each packet, may be stitched or otherwise joined together, and may be part of a discrete roll of packets for single and/or daily dosing. In some embodiments, the dosing device may be configured to dispense selections of products into multiple container types, each container type being sized for each daily dosing unit.

The belt accumulator 406 may be configured to receive the first end of the belt and to accumulate sections of the belt including packets that contain selections of the products from the dosing device 404. The belt may be separated into segments by the belt separator 418. Each of the segments may correspond to a supply period and each of the drug packets within each of the segments corresponds to a drug dose event within the supply period for the multi-drug regimen. A supply period, by way of example and not limitation, may correspond to a time during which an amount of medicine can be taken as prescribed. Pharmacies may distribute prescribed medicine for a supply period. Examples of supply periods include, but are not limited to, a 7-day supply, 14-day supply, 21-day supply, 30-day supply, 60-day supply and 90-day supply. The belt accumulator 406 may be configured to accumulate the segments of the belt into belt rolls such that, for each of the belt rolls, a first segment end is on an interior of the belt roll and a second segment end is on an exterior of the belt roll. The separation of the belt may occur before the accumulation process begins to form the belt roll, after the belt roll has been formed or the majority of the belt roll has been formed, or after the belt roll has begun to be formed but before the majority of the belt roll has been formed. In an example embodiment, the last dose is interior in the roll and the first dose is at the free, outer end of the segment of the roll. The equipment may be designed to perform the separation when the belt is temporarily stopped or slowed, or may be performed when the belt is continuously moving. There are a number of mechanisms that may be designed to accumulate the packets. For example, the belt accumulator 406 may include an accumulator fork 407 and a roll pusher 409. The accumulator fork may be configured to rotate about a fork axis such that the belt is caused to be drawn over an outer portion of the accumulator fork to form a belt roll. The accumulator fork may include two or more tines spaced from each other to engage an end of a segment. The end of the belt roll is positioned between two tines and is held thereby during creation of the roll. At least one of the tines is radially offset from the fork axis. The belt roll may include a 7-day supply, 14-day supply, 21-day supply, 30-day supply, 60-day supply and 90-day supply of daily dosing units/packets, by way of example and not limitation. The number of packets in the belt roll may correspond to other supply periods or portions of supply periods. A supply period may include one belt or may include multiple belts. For example, a 60-day supply period may be provided in two 30-day belts of packets, or a multi-week supply (e.g. 14-day, 21-day, 28-day and the like) may be provided in multiple 7-day belts of packets such each roll corresponds to a week. The roll pusher may be configured to displace the belt roll such that the belt roll may be removed from the accumulator fork and may be caused to drop to the bagger 426. The roll pusher may move to push the belt roll off of the fork. The fork may be moved to push the belt roll against roll pusher until the belt roll drops off the fork. In this embodiment, the accumulator fork may be caused to rotate by a servo motor connected to the accumulator fork and configured to monitor a number of rotations of the accumulator fork. The servo motor may be communicatively connected to the product selection order filling system 400 and configured to communicate the number of rotations of the accumulator fork such that the product selection order filling system 400 may determine that a number of the packets corresponding to a specific order is correct based on the number of rotations and data received from the inspection assembly 416. In another example, a dual paddle design may be used instead of the fork. In some embodiments, a bar code reader of the inspection assembly 416 is in communication with the servo motor and the product selection order filling system 400 to validate each prescription order type and number of packets.

The belt tensioner 408 may be configured to generate an amount of tension in the belt between the dosing device 404 and the belt accumulator 406 during operation of the product selection order filling system 400. The amount of tension in the belt may be configured to facilitate causing the packets to be maintained in a substantially parallel relationship with at least a portion of the material transport assembly 412 between the belt tensioner 408 and the belt accumulator 406. There are a number of mechanisms that may be designed to provide a desired amount of tension in the belt. For example, the belt tensioner 408 may include two outer rollers positioned against a lower surface of the belt, and an inner roller positioned against an upper surface of the belt, the upper surface opposite the lower surface of the belt. A biasing member may cause the outer rollers to be moved apart from the inner roller by a roller distance such that the amount of tension in the belt between the dosing device 404 and the belt accumulator 406 is a predetermined amount. Various web tension control designs may be implemented to maintain a desired amount of tension on the belt. For example, additional rolls may be included to help take up tension. The web tension control designs may be configured to allow accumulation and the ability to have either the upstream side or downstream side running while the other is down. The web tension control designs may be closed loop to control the tension based on measured web tension. Web tension measurements may be provided by measuring tension using a load cell or measuring a position of a roll or rolls (e.g. one or more dancer rolls). For example, a tension estimation device 410 may be connected to the order processing device 402 and configured to estimate the tension in the belt. In this embodiment, the tension estimation device 410 may be positioned vertically above the inner roller and may be an ultrasonic proximity roller level sensor configured to determine the level, or position, of the inner roller relative to the positions of the outer rollers to determine a distance between the inner roller and the outer rollers. In some embodiments, the tension estimation device 410 may be at least one of a visual sensor, a magnetic proximity sensor, and a laser proximity sensor. Using the distance between the inner roller and the outer rollers, the tension estimation device 410 and the order processing device 402 may be configured to estimate an amount of tension in the belt, and the order processing device 402 may be configured to change the positions of the inner roller and the outer rollers to cause a predetermined amount of tension to be present in the belt during operation of the product selection order filling system 400. In some embodiments, the predetermined amount of tension in the belt is a range of allowable tension values. A container identifier device 414 may be configured to associate an identifier with each of the packets and may be positioned to associate the identifier with each of the packets between the dosing device 404 and the belt accumulator 406. In some embodiments, the container identifier device 414 may be is a bar code printer. In some embodiments, the container identifier device 414 may include a laser that marks a packet containing laser responsible materials.

In this embodiment, the material transport assembly 412 may be configured to facilitate the belt moving between the dosing device 404 and the belt accumulator 406. More specifically, the material transport assembly may extend along at least a portion of the belt between the dosing device 404 and the belt accumulator and 406 and may include a vacuum conveyor configured to constrain lateral motion of the belt during operation of the product selection order filling system 400. For example, the vacuum conveyor may be used to hold the belt on the conveyor and provide a pause for the belt separator to separate the belt during continuous operation of dispensing packets. In some embodiments, the material transport assembly 412 may include a conveyor configured to retain at least a portion of the belt against a surface of the conveyor during operation of the product selection order filling system 400.

The inspection assembly 416 may include a bar code reader, an index position sensor, an imager assembly, and a scale. The bar code reader may be configured to determine literature that is associated with the selections of product that are contained within each of the packets such that the determined literature may be included with the completed belt of packets. The index position sensor may be configured to determine a position of each of the packets between the dosing device 404 and the belt accumulator 406. The imager assembly may include a transparent, or substantially transparent, packet support configured to support a first portion of the belt, and an imaging device. The imaging device may be configured to image, through the packet support, each of the packets of the belt of the packets during operation of the product selection order filling system 400. For example, the imaging device may include at least one of a vision system and an ultrasonic sensor configured to detect product selections in the packets. A suitable imaging device may include a Cognex™ vision system. The scale may be configured to weigh at least a second portion of the belt during operation of the product selection order filling system 400. In some embodiments, the scale may be configured to weigh a completed roll of the belt after it has been accumulated and is ready for packing or other disposition. In some embodiments, the scale may be a Mettler™ Toledo scale.

In this embodiment, the belt separator 418 may be configured to separate the belt into a first section including a first portion of the packets containing selections of the products and a second section including a second portion of the packets containing selections of the products. The belt separator 418 may include a blade or knife configured to cut through portions of the packets, e.g., a web between adjacent packets at an end of one segment and the beginning of another segment. The first portion and the second portion may include predetermined numbers of the packets corresponding to a predetermined supply period of the selections of the products. In an example embodiment, the first portion may include a number of packets corresponding to a fourteen-day supply of product selection daily dosage units for a first patient, and the second portion may include a twenty-one day supply of product selection daily dosage units for a second patient. The system may be designed to separate the belt using other mechanisms. By way of example and not limitation, the separation may be provided by a die cut roller or laser cutter.

The adhesive applicator 420 may be configured to apply an adhesive to a second end of the first section of the belt such that the second end of the first section of the belt is caused to adhere to at least a portion of one of the upper surface and the lower surface of the first section of the belt on the belt accumulator 406. The belt roll may be delivered to the packing area, or any other area that facilitates operation of the pharmacy order processing system 400 as described herein following application of the adhesive to the belt roll.

The box unit-of-use device 422 may be configured to place unit-of-use pharmaceutical products in containers for use by the patient and to facilitate shipment of the pharmaceutical products. The unit-of-use chute 434 may be configured to direct containers from the box unit-of-use device 422 to the bagger 426. The bottle accumulator 424 is configured to accumulate containers containing pharmaceuticals for marrying with additional portions of a prescription order for packing and shipping. The bottle chute 432 is configured to direct containers from the bottle accumulator to the bagger 426. The bagging area 438 includes the bagger 426 and the bagger scale 436. The folded paper/envelope feeder device 428 is configured to feed literature to the folded paper/pick and place device 430. The folded paper/pick and place device 430 is configured to pick literature from the folded paper/envelope feeder device 428 and to place the retrieved literature with an associated prescription order for bagging by the bagger 426. The bagger 426 is configured to bag the completed belts, the containers, the box unit-of-use products, and the literature for shipping as a prescription order. Bagger scale 436 is configured to weigh the completed prescription orders to verify the weight of each prescription order. The illustrated embodiment refers to a bagger 426. It is noted that the bagger is a type of package device configured to box, bag or otherwise package the belt rolls and other products.

Figure 7:
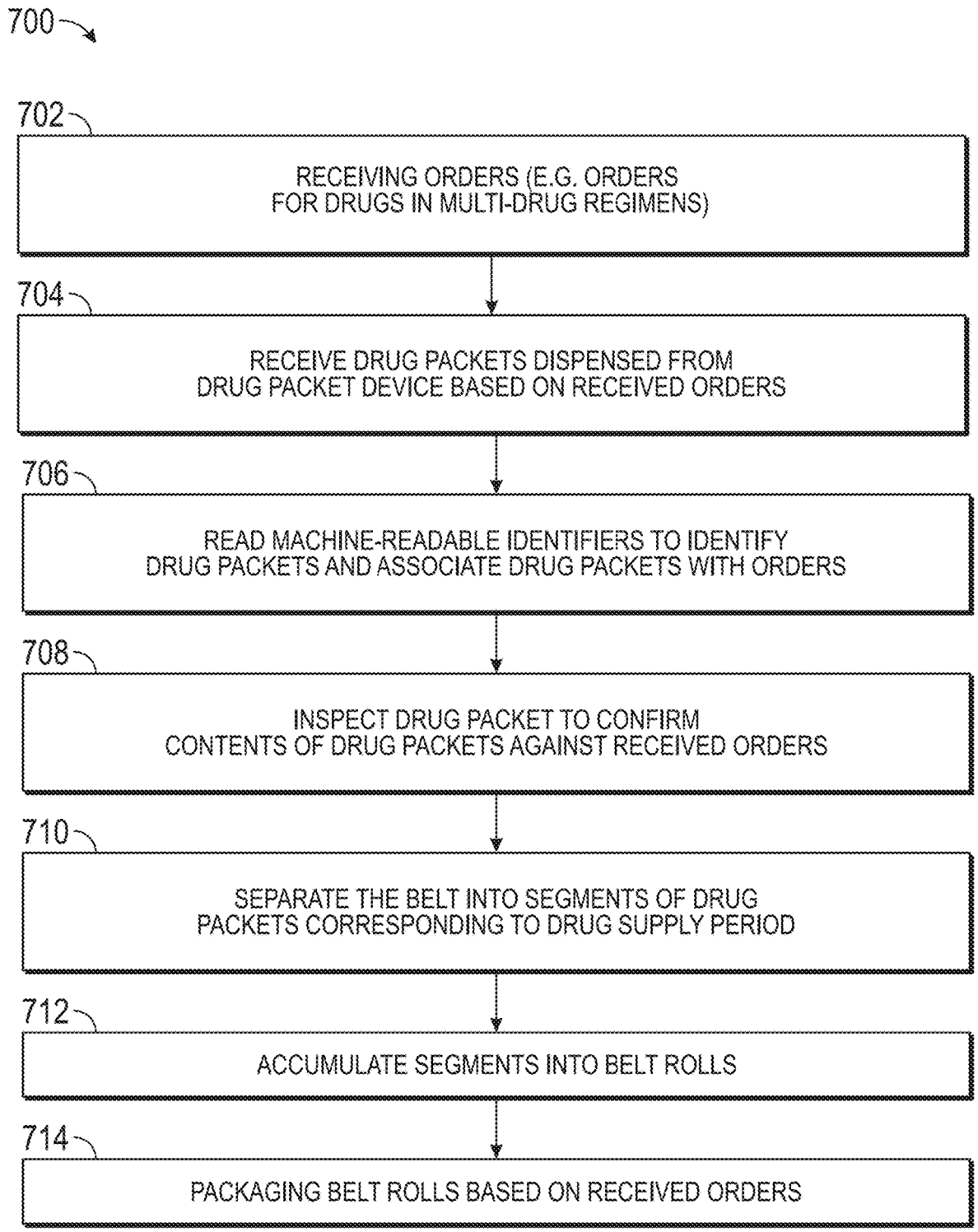
FIG. 7 illustrates, by way of example and not limitation, a process flow illustrating an embodiment of a method for filling at least a portion of a pharmaceutical order using a product selection order filling system.

FIG. 7 illustrates, by way of example and not limitation, a process flow illustrating an embodiment of a method for filling at least a portion of a pharmaceutical order using a product selection order filling system. Pharmaceutical orders may be received using an order processing device 702. The pharmaceutical orders may include orders for drugs used in multi-drug regimens, wherein each of the multi-drug regimens has a plurality of scheduled dosing event. Drug packets, which may have been dispensed from a drug packet device based on the received pharmaceutical orders, may be received 704. The drug packets may be dispensed as a belt of drug packets in which adjacent drug packets in the belt are connected. Each of the drug packets may correspond to one of the plurality of scheduled dosing events. Each of the drug packets may contain one or more of the drugs used in the multi-drug regimen for one of the plurality of scheduled dosing events. Each of the drug packets may have a machine-readable identifier identifying each of the drug packets dispensed from the drug packet dispensing device. The machine-readable identifiers in the belt may be automatically read to identify drug packets and associate the drug packets with the received orders 706. The drug packets may be automatically inspected, using an inspection assembly, to confirm contents of the drug packets against the received orders 708. The belt may be automatically separated into segments of drug packets. Each of the segments may correspond to a supply period and each of the drug packets within each of the segments may correspond to a drug dose event for the multi-drug regimen within the supply period. The segments of the belt may be automatically accumulated into belt rolls such that, for each of the belt rolls, a first segment end is on an interior of the belt roll and a second segment end is on an exterior of the belt roll 712. The belt rolls may be packaged (e.g. bagged) based on the received orders 714. For example, the belt rolls may be packaged with other prescription and/or non-prescription products based on the received orders.

Figure 8:
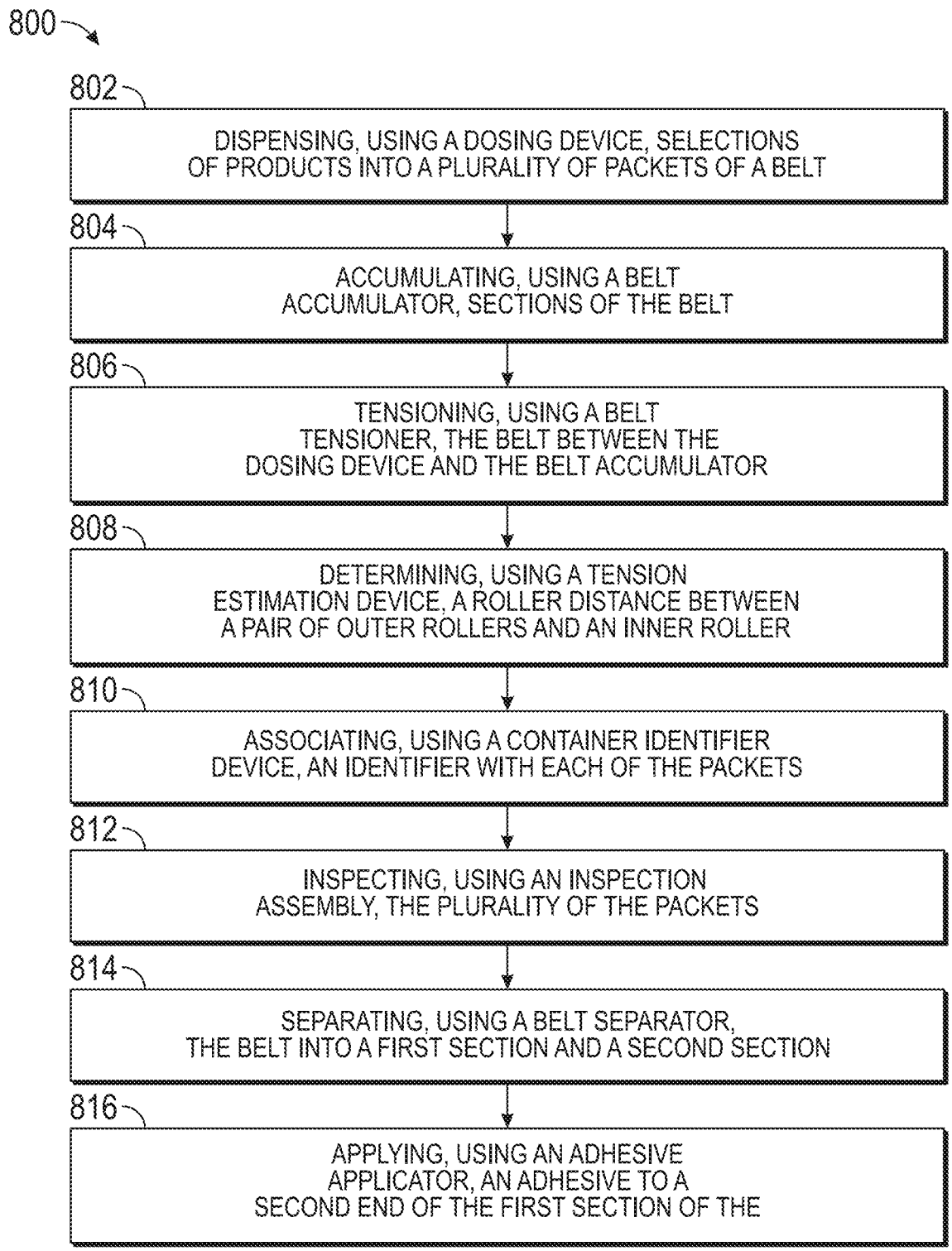
FIG. 8 illustrates, by way of example and not limitation, another process flow illustrating an embodiment of a method for filling at least a portion of a pharmaceutical order using a product selection order filling system.

FIG. 8 illustrates, by way of example and not limitation, another process flow illustrating an embodiment of a method for filling at least a portion of a pharmaceutical order using a product selection order filling system. At block 802, selections of products are dispensed, using for example the dosing device 404 described above, into multiple packets, wherein each of the packets is connected to at least one other packet to form a belt of the packets having a first end and a second end. At block 804, sections of the belt including packets containing the selections of the products are accumulated, using for example the belt accumulator 406 described above, from the dosing device 404, The belt accumulator 406 may include an accumulator fork configured to rotate about an axis of the fork such that the belt is caused to be drawn over an outer portion of the accumulator fork to form a belt roll. At block 806, the belt between the dosing device and the belt accumulator 406 is tensioned using the belt tensioner 408. In some embodiments, the belt tensioner 408 includes two outer rollers positioned against a lower surface of the belt and an inner roller positioned against an upper surface of the belt. The upper surface may be opposite the lower surface. A biasing member may cause the outer rollers to be moved apart from the inner roller by a roller distance such that the amount of tension in the belt between the dosing device 404 and the belt accumulator 406 is a predetermined amount. At block 808, a determination of the roller distance may be made. The determination may be made, for example, by the tension estimation device 410. An association of an identifier with each of the packets is made at block 810. Then association may be made by using, for example, the container identifier device 414. At block 812, an inspection of the packets is made. The inspection may be made by the inspection assembly 416 or otherwise. At block 814, the belt is separated into a first portion including a first set of the packets containing first selections of the products and a second portion including a second set of the packets containing second selections of the products. The operations at block 814 may be performed by the belt separator 418. In some embodiments, the belt separator 418 includes a knife and the first section and the second section include predetermined numbers of the packets corresponding to a predetermined supply period of the selections of the products. At block 816, an adhesive is applied to a second end of the first portion of the belt such that the second end of the first portion of the belt is caused to adhere to at least a portion of one of the upper surface and the lower surface of the first portion of the belt on the belt accumulator 406. The operations performed at block 816 may be performed by the adhesive applicator 420 or otherwise.

Figure 9:
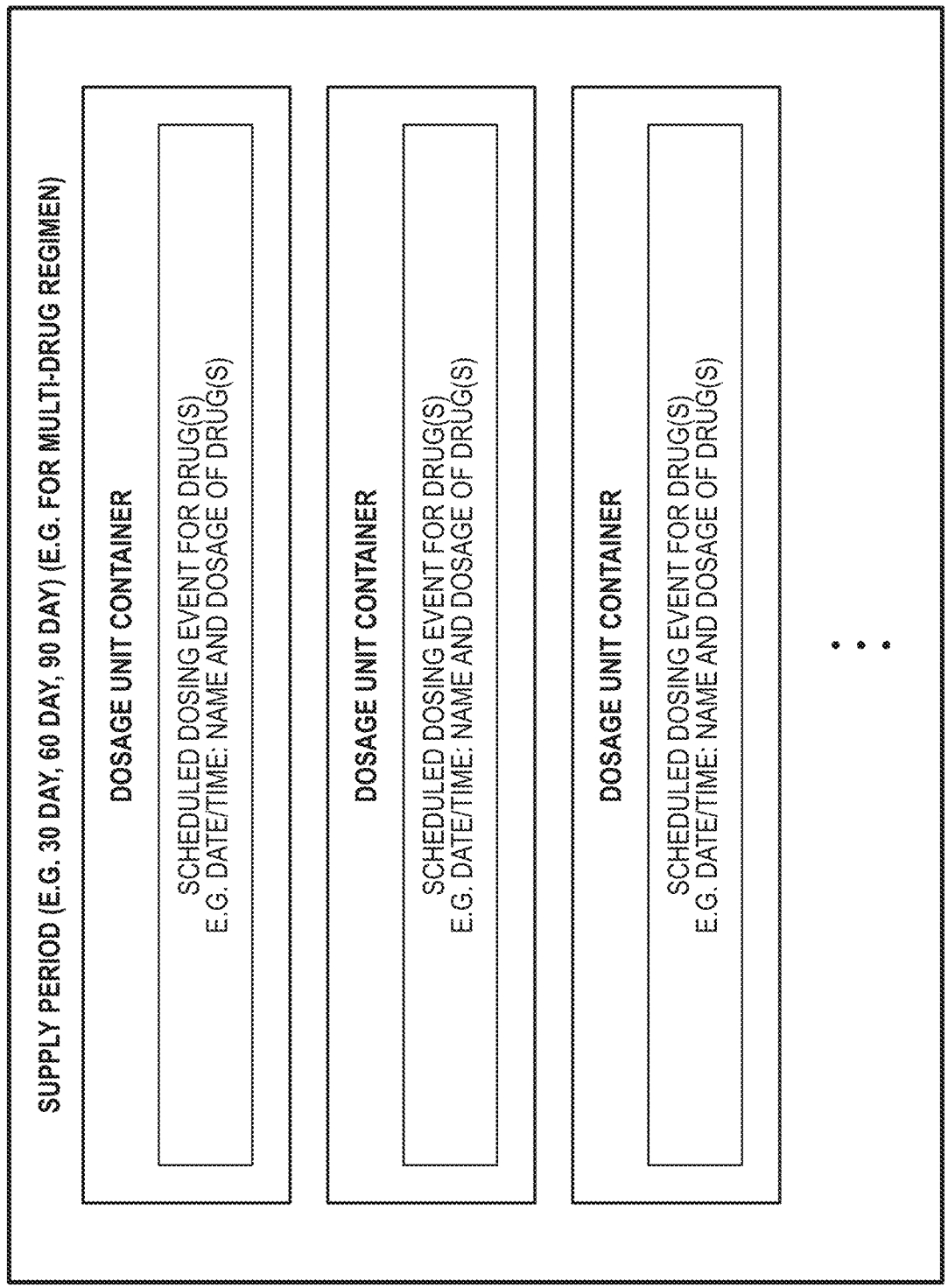
FIG. 9 illustrates, by way of example and not limitation, a plurality of dosage unit containers connected together.

FIG. 9 illustrates, by way of example and not limitation, a plurality of dosage unit containers that contain drug(s) for a scheduled dosing event for a supply period of a multi-drug regimen. A multi-drug regimen may include at least two different types of drugs that are to be administered at different times over the course of a day. By way of example and not limitation, a first drug and second drug may be taken in the morning at breakfast, a third drug may be taken around noon, and the first and a fourth drug may be taken in the evening. This example has three scheduled dosing events (e.g. morning, noon and evening) per day. In another example, the dosing regimen may include one dosing event per day (or over another time period). The dosing regimen may include two or more dosing events (e.g. 2, 3, 4, 5, 6, 7 or 8 events) per day (or over another time period). Each dosing event may include one or more of the drugs used within the multi-drug regimen. Different dosing events may include different drug(s). The drug(s) for each dosing event may be within its own separate container, referred to herein as a dosage unit container. The dosage unit container may be or may include a drug package from the belt. In an example embodiment, the dosage unit containers are consecutively connected to the next dose in a schedule of individual doses. A package may include the drugs ordered over the course of a supply period (e.g. 30-day supply of medicine, 60-day supply medicine or 90-day supply of medicine), and thus may include a corresponding number of the dosage unit containers over the course of the supply period.

In one aspect, a product selection order filling system includes an order processing device to receive orders, a dosing device, a belt accumulator, a belt tensioner, a tension estimation device, a material transport assembly, a container identifier, an inspection assembly, a belt separator, and an adhesive applicator. The dosing device is connected to the order processing device and is configured to dispense selections of products into multiple packets, wherein each of the packets is connected to at least one other packet to form a belt of multiple packets having a first end and a second end. The belt accumulator is configured to receive the first end of the belt and to accumulate sections of the belt including packets containing the selections of the products from the dosing device, wherein the belt accumulator includes an accumulator fork configured to rotate about a fork axis such that the belt is caused to be drawn over an outer portion of the accumulator form to form a belt roll. The belt tensioner is configured to generate an amount of tension in the belt between the dosing device and the belt accumulator, wherein the belt tensioner includes two outer rollers positioned against a lower surface of the belt and an inner roller positioned against an upper surface of the belt, the upper surface opposite the lower surface, and wherein a biasing member causes the outer rollers to be moved apart from the inner roller by a roller distance such that the amount of tension in the belt between the dosing device and the belt accumulator is a predetermined amount. The tension estimation device is connected to the order processing device and is configured to estimate the tension in the belt. The material transport assembly is configured to facilitate the belt moving between the dosing device and the belt accumulator, wherein the material transport assembly includes a vacuum conveyor. The container identifier device is configured to associate an identifier with each of the packets. The inspection assembly includes a bar code reader, an index position sensor, an imager assembly, and a scale. The bar code reader determines literature associated with selections of the products within each of the packets. The index position sensor determines a position of each of the packets between the dosing device and the belt accumulator. The imager assembly includes a transparent packet support configured to support a first portion of the belt, and an imaging device configured to image, through the transparent packet support, each of the packets of the belt of the packets. The scale is configured to weight at least a second portion of the belt. The belt separator is configured to separate the belt into a first section including a first portion of the packets containing selections of the products and a second section including a second portion of the packets containing selections of the products, wherein the belt separator includes a knife, and wherein the first section and the second section include predetermined numbers of the packets corresponding to a predetermined supply period of the selections of the products. The adhesive applicator is configured to apply an adhesive to a second end of the first section of the belt such that the second end of the first section of the belt is caused to adhere to at least a portion of one of the upper surface and the lower surface of the first section of the belt on the belt accumulator.

In another aspect, a product selection order filling system includes an order processing device to receive orders, a dosing device, a belt accumulator, a belt tensioner, a material transport assembly, a container identifier, an inspection assembly, and a belt separator. The dosing device is connected to the order processing device and is configured to dispense selections of products into multiple packets, wherein each of the packets is connected to at least one other packet to form a belt of the packets having a first end and a second end. The belt accumulator is configured to receive the first end of the belt and to accumulate sections of the belt including packets containing the selections of the products from the dosing device. The belt tensioner is configured to generate an amount of tension in the belt between the dosing device and the belt accumulator. The material transport assembly is configured to facilitate the belt moving between the dosing device and the belt accumulator. The container identifier device is configured to associate an identifier with each of the packets. An inspection assembly includes at least one inspection device configured to at least one of weigh each of the packets, image each of the packets to determine the order associated with each of the packets, and image each of the packets to determine the selection of the products in each of the packets. The belt separator is configured to separate the belt into a first section including a first portion of the packets and a second section including a second portion of the packets.

The term "based on" or using, as used herein, reflects an open-ended term that can reflect others elements beyond those explicitly recited. Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The embodiments of the present disclosure generally provide for multiple circuits or other electrical devices, which can be used in units, modules, systems, and sub-systems and the like. All references to such and the functionality provided by each are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical/operational implementation that is desired. It is recognized that any circuit or other electrical device disclosed herein may include any number of microprocessors, discrete circuit components, integrated circuits, memory devices (e.g., FLASH, random access memory (RAM), read only memory (ROM), electrically programmable read only memory (EPROM), electrically erasable programmable read only memory (EEPROM), or other suitable variants thereof, etc.) and instructions (e.g., software, etc.) which co-act with one another to perform operation(s) disclosed herein. In addition, any one or more than one electric device may be configured to execute a computer-program that is embodied in a computer readable medium that is programmed to perform any number of the functions and features as disclosed. The computer readable medium may be non-transitory or in any form readable by a machine or electrical component.

At least some portions of the present disclosure may be accomplished by using a robot. A robot can be a machine capable of carrying out a complex series of actions automatically. These complex series of actions may include picking up, orientating, positioning and/or releasing a prescription component, a pill, a container or other structure. The robot may be dedicated to a single series of movements or may be able to execute multiple series of movements. A robot may include a processor that received instructions and then executes instructions to control its movement. In another example, a robot may resemble a human being and replicate certain human movements and functions, may move location, have an articulated arm, have grasping structures that replicate fingers and do not damage containers, and the like.

Methods and systems for pharmacy order processing, including dispensing product selections into a daily dosage unit packets and inspecting, sorting, and packing the packets have been described. Although embodiments of the present disclosure have been described with reference to specific example embodiments, it will be evident that various modifications and changes may be made to these embodiments without departing from the broader spirit and scope of the embodiments of the disclosure. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks may be shown in the flowcharts, the methods may be performed continuously.

In the foregoing, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more than one steps within a method may be executed in different order (or concurrently) without altering the principles of the present disclosure. Further, although each of the embodiments is described above as having certain features, any one or more than one of those features described with respect to any embodiment of the disclosure can be implemented in and/or combined with features of any of the other embodiments, even if that combination is not explicitly described. In other words, the described embodiments are not mutually exclusive, and permutations of one or more than one embodiment with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more than one intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In this application, including the definitions below, the term 'module' or the term 'controller' may be replaced with the term 'circuit.' The term 'module' may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more than one interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuitry that, in combination with additional processor circuits, executes some or all code from one or more than one modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more than one modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The systems and methods described in this application may be partially or fully implemented by a special purpose computer created by configuring a general purpose computer to execute one or more than one particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more than one operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

Embodiments for pharmacy order processing using daily dosage unit product selection dispensing systems are described above in detail. The systems and methods of operating such systems are not limited to the specific embodiments described herein, but rather, components of systems and/or steps of the methods may be utilized independently and separately from other components and/or steps described herein. For example, the methods may also be used in combination with other systems and environments and are not limited to the environments as described herein. Rather, the embodiments can be implemented and utilized in connection with many other applications.

In this specification and the claims, reference is made to a number of terms, which shall be defined to have the following meanings:

The singular forms "a", "an", and "the" include plural references unless the context clearly dictates otherwise.

"Optional" or "optionally" means that the subsequently described event or circumstance may or may not occur, and that the description includes instances where the event occurs and instances where it does not.

The term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, cd-roms, dvds, and any other digital source such as a network or the internet, as well as yet to be developed digital means, with the sole exception being a transitory, propagating signal.

The terms "software" and "firmware" are interchangeable, and include any computer program stored in memory for execution by devices that include, without limitation, mobile devices, clusters, personal computers, workstations, clients, and servers.

The term "computer" and related terms, e.g., "computing device", are not limited to integrated circuits referred to in the art as a computer, but broadly refers to a microcontroller, a microcomputer, a programmable logic controller (plc), an application specific integrated circuit, and other programmable circuits, and these terms are used interchangeably herein.

Computer systems are described, and such computer systems include a processor and a memory. However, any processor in a computer device referred to may also refer to one or more processors wherein the processor may be in one computing device or multiple computing devices acting in parallel, such as in a cloud computing environment. Additionally, any memory in a computer device referred to may also refer to one or more memories, wherein the memories may be in one computing device or multiple computing devices acting in parallel.

A processor may include any programmable system including systems using micro-controllers, reduced instruction set circuits (risc), application specific integrated circuits (asics), logic circuits, and any other circuit or processor capable of executing the functions described herein. The above examples are example only, and are thus not intended to limit in any way the definition and/or meaning of the term "processor." The term "database" may refer to either a body of data, a relational database management system (rdbms), or to both. A database may include any collection of data including hierarchical databases, relational databases, flat file databases, object-relational databases, object oriented databases, and any other structured collection of records or data that is stored in a computer system. The above are only examples, and thus are not intended to limit in any way the definition and/or meaning of the term database. Examples of rdbms's include, but are not limited to including, Oracle® Database, Mysql, IBM® Db2, Microsoft® Sql Server, Sybase®, and Postgresql. However, any database may be used that enables the systems and methods described herein. (oracle is a registered trademark of Oracle Corporation, Redwood Shores, Calif.; IBM is a registered trademark of International Business Machines Corporation, Armonk, N.Y.; Microsoft is a registered trademark of Microsoft Corporation, Redmond, Wash.; and Sybase is a registered trademark of Sybase, Dublin, Calif.)

In some embodiments, a computer program is embodied on a computer readable medium. In other embodiments, the system is executed on a single computer system, without requiring a connection to a server computer. In still other embodiments, the system is run in a Windows® environment (windows is a registered trademark of Microsoft corporation, Redmond, Wash.). In yet another embodiment, the system is run on a mainframe environment and a Unix® server environment (Unix is a registered trademark of x/open company limited located in reading, Berkshire, United Kingdom). The application is flexible and designed to run in various different environments without compromising any major functionality. In some embodiments, the system includes multiple components distributed among multiple computing devices. One or more components may be in the form of computer-executable instructions embodied in a computer-readable medium.

Approximating language, as used herein throughout the specification and claims, may be applied to modify any quantitative representation that could permissibly vary without resulting in a change in the basic function to which it is related. Accordingly, a value modified by a term or terms, such as "about" and "substantially", are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise.

The inventive subject matter may be represented in a variety of different embodiments of which there are many possible permutations. Although specific features of various embodiments of the invention may be shown in some drawings and not in others, this is for convenience only. In accordance with the principles of the invention, any feature of a drawing may be referenced and/or claimed in combination with any feature of any other drawing. This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

In yet another aspect, a method of filling an order with a selection of products includes dispensing, using a dosing device, selections of products into multiple packets, wherein each of the packets is connected to at least one other packet to form a belt of the packets having a first end and a second end. The method also includes accumulating, using a belt accumulator, sections of the belt including packets containing the selections of the products from the dosing device, wherein the belt accumulator includes an accumulator fork configured to rotate about a fork axis such that the belt is caused to be drawn over an outer portion of the accumulator fork to form a belt roll. The method further including tensioning, using a belt tensioner, the belt between the dosing device and the belt accumulator wherein the belt tensioner includes two outer rollers positioned against a lower surface of the belt and an inner roller positioned against an upper surface of the belt, the upper surface opposite the lower surface, and wherein a biasing member causes the outer rollers to be moved apart from the inner roller by a roller distance such that an amount of tension in the belt between the dosing device and the belt accumulator is a predetermined amount. The method includes determining, using a tension estimation device, the roller distance. The method also includes associating, using a container identifier device, an identifier with each of the packets. The method further includes inspecting, using an inspection assembly, the belt of the packets. The method includes separating, using a belt separator, the belt into a first section including a first portion of the packets containing selections of the products and a second section including a second portion of the packets containing selections of the products, wherein the belt separator includes a knife and wherein the first section and the second section include predetermined numbers of the packets corresponding to a predetermined supply period of the selections of the products. The method further includes applying, using an adhesive applicator, an adhesive to a second end of the first section of the belt such that the second end of the first section of the belt is caused to adhere to at least a portion of one of the upper surface and the lower surface of the first section of the belt on the belt accumulator.

Various refinements exist of the features noted in relation to the above-mentioned aspects. Further features may also be incorporated in the above-mentioned aspects as well. These refinements and additional features may exist individually or in any combination. For instance, various features discussed below in relation to any of the illustrated embodiments may be incorporated into any of the above-described aspects, alone or in any combination.

The above detailed description is intended to be illustrative, and not restrictive. The scope of the disclosure should, therefore, be determined with references to the appended claims, along with the full scope of equivalents to which such claims are entitled.

What is claimed is:

1. An order-filling system, comprising:
a drug packet dispensing device configured to:
communicate with an order processing device to receive multi-drug regimen orders with the multi-drug regimens having a plurality of scheduled dosing events for administering drug doses and at least one of the plurality of scheduled dosing events is for administering doses for at least two different drugs, and
dispense drug packets based on the multi-drug regimen orders, wherein the drug packets are dispensed as a belt of drug packets in which adjacent drug packets in the belt are connected, the drug packets in the belt respectively correspond to the plurality of scheduled dosing events, the drug packets dispensed in the belt contain one or more of the drugs used in the multi-drug regimen, at least one of the drug packets dispensed in the belt includes the doses for the at least two different drugs, and the drug packets have a machine-readable identifier identifying each of the drug packets dispensed from the drug packet dispensing device;
a container-identifier device configured to read the machine-readable identifiers of the belt to identify drug packets and associate the identified drug packets with the multi-drug regimen orders;

an inspection assembly configured to inspect the drug packets to confirm contents of the drug packets against the received pharmaceutical orders;

a belt separator configured to separate the belt into segments of drug packets, wherein each of the segments contains multiple drug packets for a single patient and corresponds to a supply period for the single patient, and each of the drug packets within each of the segments corresponds to a drug dose event within the supply period for the multi-drug regimen;

a belt accumulator configured to accumulate the segments of the belt into belt rolls such that, for a belt roll of the belt rolls, a first segment end is on an interior of the belt roll and a second segment end is on an exterior of the belt roll;

a material transport assembly configured for use in moving the belt between the drug packet dispensing device and the belt accumulator, wherein the material transport assembly includes a web tensioner after the drug packets are filled and before the belt accumulator to control tension in the web and allow accumulation of the belt with the belt separator and the dispensing device operating differently;

a bagger to receive the belt roll and to package the belt roll for shipment;

a unit-of-use device to direct unit-of-use to the bagger with an order requiring a unit-of-use and the belt roll; and a bottle accumulator to direct a bottle to the bagger with an order requiring a prescription bottle and the belt roll, wherein the bagger includes a scale to weigh a bagged order that contains the belt roll and at least one of the bottle, the unit-of-use or both.

2. The order-filling system of claim 1, wherein the material transport assembly includes a tension estimation device to estimate the tension on the belt, and wherein the material transport assembly uses an estimate of the tension on the belt to control the web tensioner and the tension on the belt.

3. The order-filling system of claim 2, wherein the tension estimation device includes an ultrasonic proximity sensor.

4. The order-filling system of claim 2, wherein the material transport assembly includes a vacuum conveyor to hold the belt of drug packets on the conveyor and provide a pause for the belt separator to separate the belt.

5. The order-filling system of claim 2, wherein the belt is flexible and continuous.

6. An order-filling system, comprising:
a drug packet dispensing device configured to:
communicate with an order processing device to receive multi-drug regimen orders with the multi-drug regimens having a plurality of scheduled dosing events for administering drug doses and at least one of the plurality of scheduled dosing events is for administering doses for at least two different drugs, and dispense drug packets based on the multi-drug regimen orders, wherein the drug packets are dispensed as a belt of drug packets in which adjacent drug packets in the belt are connected, the drug packets in the belt respectively correspond to the plurality of scheduled dosing events, the drug packets dispensed in the belt contain one or more of the drugs used in the multi-drug regimen, at least one of the drug packets dispensed in the belt includes the doses for the at least two different drugs, and the drug packets have a machine-readable identifier identifying each of the drug packets dispensed from the drug packet dispensing device;

a container-identifier device configured to read the machine-readable identifiers of the belt to identify drug packets and associate the identified drug packets with the multi-drug regimen orders;

an inspection assembly configured to inspect the drug packets to confirm contents of the drug packets against the received pharmaceutical orders;

a belt separator configured to separate the belt into segments of drug packets, wherein each of the segments contains multiple drug packets for a single patient and corresponds to a supply period for the single patient, and each of the drug packets within each of the segments corresponds to a drug dose event within the supply period for the multi-drug regimen, the supply period including a multiple-day supply of drugs;

a belt accumulator configured to accumulate the segments of the belt into belt rolls such that, for a belt roll of the belt rolls, a first segment end is on an interior of the belt roll and a second segment end is on an exterior of the belt roll, the belt accumulator including a fork to engage an end of the segment of the belt to wind the segment into the belt roll;

a material transport assembly configured for use in moving the belt between the drug packet dispensing device and the belt accumulator, wherein the material transport assembly includes a web tensioner after the drug packets are filled and before the belt accumulator to control tension in the web and allow accumulation of the belt with the belt separator and the dispensing device operating differently; and a bagger to receive the belt roll and to package the order including the belt roll for shipment;

a unit-of-use device to direct unit-of-use to the bagger with an order requiring a unit-of-use and the belt roll; and a bottle accumulator to direct a bottle to the bagger with an order requiring a prescription bottle and the belt roll, wherein the bagger includes a scale to weigh a bagged order that contains the belt roll and at least one of the bottle, the unit-of-use or both.

7. The order-filling system of claim 6, wherein the web tensioner includes two outer rollers and an inner roller positioned after the drug packet dispensing device, wherein the segment has opposing first and second sides, and the inner roller is configured to contact a first side of the segment and the two outer rollers are configured to contact the second side of the segment, and wherein a biasing member is configured to provide the segment with a set tension.

8. The order-filling system of claim 6, wherein a speed of the belt being dispensed from the drug packet dispensing device and the speed of the belt as it is accumulated by the belt accumulator varies, wherein the system further comprises a tension estimation device configured to estimate the tension in the belt between the drug packet dispensing device and the belt accumulator based at least in part on the received pharmaceutical orders.

9. The order-filling system of claim 6, wherein the inspection assembly includes:
an index position sensor configured to determine a position of each of the packets between the dosing device and the belt accumulator; and
at least one of:

an imager assembly including a transparent packet support configured to support a first portion of the belt, and an imaging device configured to image, through the transparent packet support, each of the plurality of the packets; or an ultrasonic sensor configured for use in confirming presence of pills within the drug packets.

10. The order-filling system of claim 6, wherein the inspection assembly further includes a scale configured to weigh at least the segment, or an ultrasonic sensor configured for use in confirming presence of pills within the drug packets.

11. The order-filling system of claim 6, further comprising a literature feed device configured to feed literature to the package device to be packaged with the belt roll.

12. The order-filling system of claim 6, wherein the fork includes tines and an axis of rotation, wherein the tines are offset from the axis of rotation.

13. The order-filling system of claim 6, wherein the fork includes tines, the system further is configured to push the belt roll off of the tines, and the system includes a literature machine configured to provide printed material to be packaged with the belt roll pushed off of the tines.

14. An order-filling system, comprising:
a drug packet dispensing device configured to:
communicate with an order processing device to receive multi-drug regimen orders with the multi-drug regimens having a plurality of scheduled dosing events for administering drug doses and at least one of the plurality of scheduled dosing events is for administering doses for at least two different drugs, and dispense drug packets based on the multi-drug regimen orders, wherein the drug packets are dispensed as a belt of drug packets in which adjacent drug packets in the belt are connected, the drug packets in the belt respectively correspond to the plurality of scheduled dosing events, the drug packets dispensed in the belt contain one or more of the drugs used in the multi-drug regimen, at least one of the drug packets dispensed in the belt includes the doses for the at least two different drugs, and the drug packets have a machine-readable identifier identifying each of the drug packets dispensed from the drug packet dispensing device;

a container-identifier device configured to read the machine-readable identifiers of the belt to identify drug packets and associate the identified drug packets with the multi-drug regimen orders;

an inspection assembly configured to inspect the drug packets to confirm contents of the drug packets against the received pharmaceutical orders;

a belt separator configured to separate the belt into segments of drug packets, wherein each of the segments contains multiple drug packets for a single patient and corresponds to a supply period for the single patient, and each of the drug packets within each of the segments corresponds to a drug dose event within the supply period for the multi-drug regimen;

a belt accumulator configured to accumulate the segments of the belt into belt rolls such that, for a belt roll of the belt rolls, a first segment end is on an interior of the belt roll and a second segment end is on an exterior of the belt roll;

a material transport assembly configured for use in moving the belt between the drug packet dispensing device and the belt accumulator, wherein the material transport assembly includes a web tensioner after the drug packets are filled and before the belt accumulator to control tension in the web and allow accumulation of the belt with the belt separator and the dispensing device operating differently;

a bagger to receive the belt roll and to package the belt roll for shipment; and a bottle accumulator to direct a bottle to the bagger with an order requiring a prescription bottle and the belt roll, wherein the bagger includes a scale to weigh a bagged order that contains the belt roll, the bottle, or both.

15. The order-filling system of claim 14, wherein the material transport assembly includes a tension estimation device to estimate the tension on the belt, and wherein the material transport assembly uses an estimate of the tension on the belt to control the web tensioner and the tension on the belt.

16. The order-filling system of claim 15, wherein the tension estimation device includes an ultrasonic proximity sensor.

17. The order-filling system of claim 15, wherein the material transport assembly includes a vacuum conveyor to hold the belt of drug packets on the conveyor and provide a pause for the belt separator to separate the belt.

18. The order-filling system of claim 17, wherein the belt is flexible and continuous.

\* \* \* \* \*